(12) United States Patent
Graham et al.

(10) Patent No.: US 10,226,470 B2
(45) Date of Patent: Mar. 12, 2019

(54) DGAT1 INHIBITION FOR TREATMENT OF DEMYELINATING INFLAMMATORY DISEASE

(71) Applicant: The Board of Trustees of the Leland Stanford Junior University, Stanford, CA (US)

(72) Inventors: Kareem Graham, Atlanta, GA (US); Eugene C. Butcher, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/311,712

(22) PCT Filed: Jun. 2, 2015

(86) PCT No.: PCT/US2015/033799
§ 371 (c)(1),
(2) Date: Nov. 16, 2016

(87) PCT Pub. No.: WO2015/187704
PCT Pub. Date: Dec. 10, 2015

(65) Prior Publication Data
US 2017/0095483 A1   Apr. 6, 2017

Related U.S. Application Data

(60) Provisional application No. 62/007,331, filed on Jun. 3, 2014.

(51) Int. Cl.
| | | |
|---|---|---|
| *A61K 31/535* | (2006.01) |
| *A61K 31/5383* | (2006.01) |
| *A61K 45/06* | (2006.01) |
| *A61K 31/196* | (2006.01) |
| *A61K 31/4965* | (2006.01) |
| *A61K 31/519* | (2006.01) |
| *A61K 31/426* | (2006.01) |

(52) U.S. Cl.
CPC ........ *A61K 31/5383* (2013.01); *A61K 31/196* (2013.01); *A61K 31/426* (2013.01); *A61K 31/4965* (2013.01); *A61K 31/519* (2013.01); *A61K 45/06* (2013.01)

(58) Field of Classification Search
USPC ........................................................ 514/230.5
See application file for complete search history.

(56) References Cited

U.S. PATENT DOCUMENTS

2008/0015227 A1 *  1/2008  Kym ................... C07C 275/42
                                                        514/326
2008/0090876 A1 *  4/2008  Cheng ................ A61K 31/382
                                                        514/337

FOREIGN PATENT DOCUMENTS

WO      2005/044250 A1    5/2005

OTHER PUBLICATIONS

DeVita et. al. (Journal of Medicinal Chemistry (2013) 56:9820-9825) (Year: 2013).*
Devita et al., "Current Status of the Research and Development of Diacylglycerol O-Acyltransferase 1 (DGAT1) Inhibitors", Journal of Medicinal Chemistry. Aug. 6, 2013. pp. 9820-9825, vol. 56, ACS Publications, Washington, DC.

* cited by examiner

*Primary Examiner* — Marcos L Sznaidman
(74) *Attorney, Agent, or Firm* — Pamela J. Sherwood; Bozicevic, Field & Francis LLP

(57) ABSTRACT

Methods are provided for treating autoimmune disease in a subject by inhibiting the activity of DGAT1.

4 Claims, 16 Drawing Sheets

DGAT1 INHIBITION FOR TREATMENT OF DEMYELINATING INFLAMMATORY DISEASE

CROSS REFERENCE

This application claims benefit and is a 371 application of PCT Application No. PCT/US2015/033799, filed Jun. 2, 2015, which claims benefit of U.S. Provisional Patent Application No. 62/007,331, filed Jun. 3, 2014, which applications are incorporated herein by reference in their entirety.

INTRODUCTION

Multiple Sclerosis (MS) is an autoimmune disease of the central nervous system (CNS) of unknown etiology that affects ~400,000 Americans. Multiple sclerosis (MS) is characterized by disseminated patches of demyelination in the brain and spinal cord. Common symptoms include visual and oculomotor abnormalities, paresthesias, weakness, spasticity, urinary dysfunction, and mild cognitive impairment. Typically, neurologic deficits are multiple, with remissions and exacerbations gradually producing disability. Neuromyelitis optica (NMO), previously considered a variant of MS, is now recognized as a separate disorder.

MS is believed to involve an immunologic mechanism. In MS, myelin reactive T cells enter into the brain and spinal cord and mediate destruction of the myelin sheath surrounding neurons resulting in progressive motor dysfunction and eventual paralysis. Current treatment strategies include switching the pro-inflammatory Th1 T cell phenotype to an anti-inflammatory Th2 response, preventing encephalitogenic T cells from extravasating into the brain, inducing T cell tolerance, anergy or apoptosis, and repairing or replacing damaged CNS cells, such as neurons and oligodendrocytes.

MS is characterized by varied CNS deficits, with remissions and recurring exacerbations. Although MS may progress and regress unpredictably, there are typical patterns of progression, including relapsing-remitting, primary progressive, secondary progressive, and progressive relapsing. MS is suspected in patients with optic neuritis, INO, or other symptoms that suggest MS, particularly if deficits are multifocal or intermittent. If MS is suspected, brain MRI and spinal MRI are done.

Most patients who have a clinically isolated syndrome eventually develop MS, with a second lesion becoming evident or MRI detecting a lesion, usually 2 to 4 yr after the initial symptoms begin. Treatment with disease-modifying drugs can delay this progression. If patients have a radiologically isolated syndrome, progression to MS is a risk, but further study of this risk is needed.

Treatment includes corticosteroids for acute exacerbations, and immunomodulators to prevent exacerbations. Goals include shortening acute exacerbations, decreasing frequency of exacerbations, and relieving symptoms; maintaining the patient's ability to walk is particularly important. Immunomodulatory therapy, such as interferons (IFNs) or glatiramer, decreases the frequency of acute exacerbations and delays eventual disability. Oral immunomodulatory drugs fingolimod, teriflunomide, and dimethyl fumarate, have recently become available for the treatment of relapsing forms of MS. The immunosuppressant mitoxantrone may be helpful, particularly for progressive MS that is refractory to other treatments. Natalizumab, an anti-$\alpha_4$ integrin antibody, inhibits passage of leukocytes across the blood-brain barrier; given as a monthly infusion, it reduces number of exacerbations and new brain lesions but may increase the risk of progressive multifocal leukoencephalopathy. If immunomodulatory drugs are ineffective, monthly IV immune globulin may help.

Immunosuppressants other than mitoxantrone (eg, methotrexate, azathioprine, mycophenolate, cyclophosphamide, cladribine) have been used for more severe, progressive MS but are controversial.

New approaches for the treatment of MS, particularly new approaches that target novel pathways and may provide for complementary or synergistic combinations with existing therapies are of great interest. The present invention addresses this need.

SUMMARY OF THE INVENTION

Methods are provided for treating autoimmune diseases associated with dysregulated numbers of regulatory T cells. In some embodiments the disease is a disease of the central nervous system, which includes without limitation, demyelinating inflammatory disease in a subject. In other embodiments the disease is a disease of the skin, e.g. psoriasis. In the methods of the invention, a DGAT1 inhibitor is administered in a dose effective to reduce the symptoms of the disease. Small molecule inhibitors of DGAT1 are available, or alternatively biologic drugs can be used, e.g. monoclonal antibodies, chimeric proteins/peptides, anti-sense oligonucleotides, and interfering RNA. In some embodiments, the treatment is effective in correcting dysregulated induction of regulatory T cells in the central nervous system. In some embodiments, the treatment is effective in decreasing mononuclear cell infiltrates within the CNS. In some embodiments, the autoimmune disease is associated with TH17 polarized T cells.

The therapeutic methods of the invention are useful for the treatment of MS and other diseases, e.g. experimental animal models such as experimental autoimmune encephalomyelitis (EAE), NMO; etc. In some embodiments, the autoimmune disease is multiple sclerosis. In some embodiments, the autoimmune disease is neuromyelitis optica.

In some embodiments of the invention, prior to treatment the individual is analyzed for identification of reduced numbers of Treg cells, e.g. by quantitating FoxP3+ cells that act on disease associated T cells; or disease associated epitopes. In other embodiments, prior to treatment the individual is analyzed for the presence of cytokines indicative of the TH1/TH17 status of the patient, e.g. IL-17, e.g. IL-17F, IL-17, IL-23, γ-IFN, etc.

In some embodiments of the invention, the effectiveness of the treatment is assessed by clinical indicia of the disease, e.g. presence of foci in the brain, gait, balance, etc. In some embodiments the effectiveness of the treatment is assessed by determining CNS T cell activity, e.g. the number and activation state of CD4+ T cells, including but not limited to TH17 polarized cells; pathogenic T effector cells; and FoxP3+ regulatory T cells.

In some embodiments a kit is provided for practice of the methods. A kit may include, without limitation, a DGAT1 inhibitor, e.g. provided in a unit dose formulation, where the dose is effective in treating demyelinating inflammatory disease in a subject. Kits may further comprise reagents for analysis of T cells involved in the disease, e.g. regulatory T cells, T effector cells, and the like.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DESCRIPTION OF THE SPECIFIC EMBODIMENTS

Figure 1:
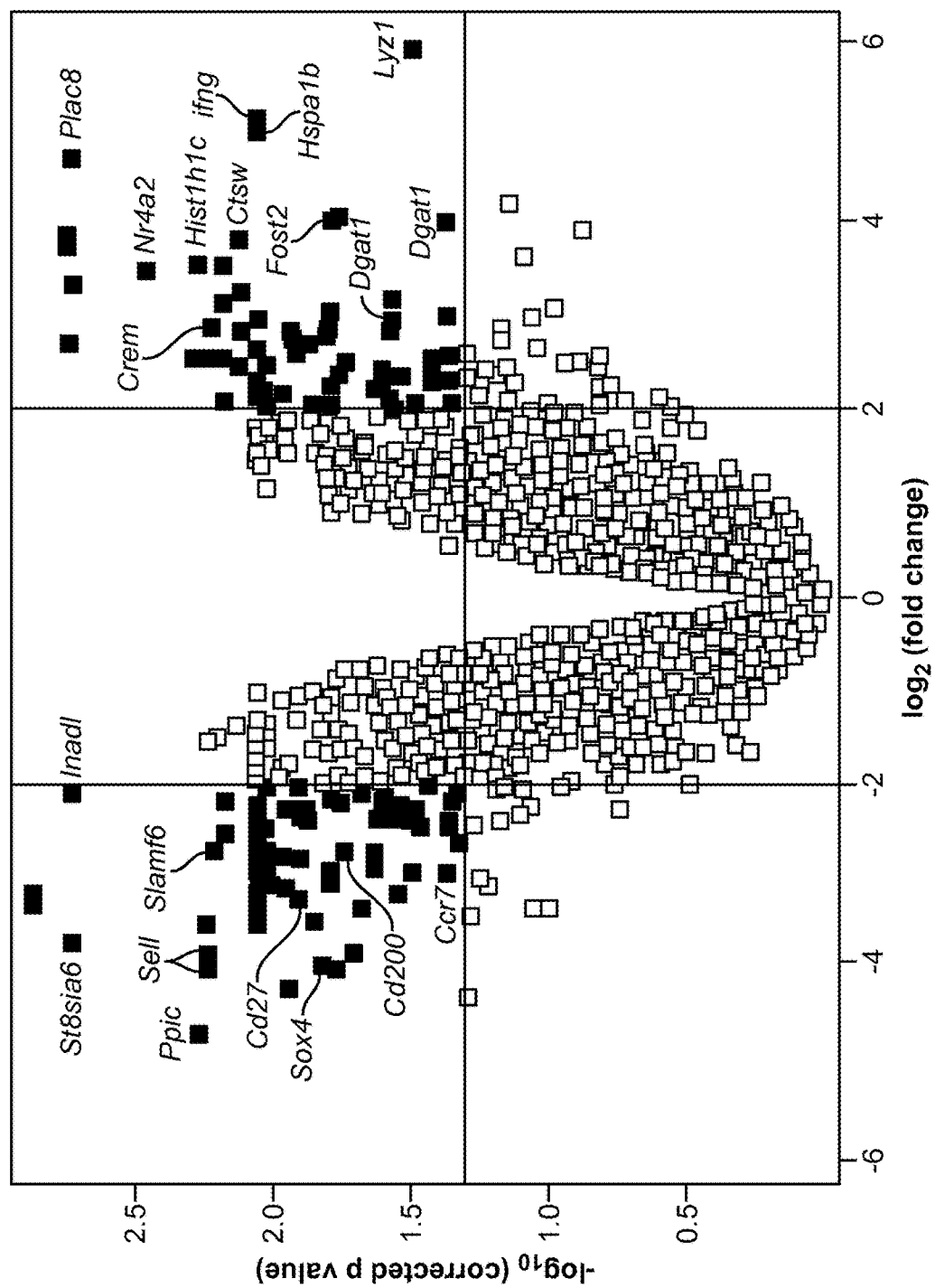
FIG. 1. Transcriptomic analysis of CNS-infiltrating memory CD4+ T cells during EAE. Transcripts in FACS-sorted memory phenotype CD4+ T cells (memCD4Ts) derived from mice with EAE were analyzed using Affymetrix gene chips. GeneSpring software was used for data analysis and visualization. (15288 probes met the selection criteria described in the Methods section.) Highly differentially expressed transcripts within CNS memCD4Ts (compared to EAE dLN memCD4Ts) are displayed in volcano plot form. Each symbol represents an individual gene; red symbols indicate transcripts that exhibited at least a fourfold difference in expression value between CNS and EAE dLN memCD4Ts.

As summarized above, the present invention is drawn to methods for treating autoimmune disease, including demyelinating inflammatory disease, psoriasis, etc. in a subject by administering an agent that antagonizes or inhibits the activity of diacylglycerol O-acyltransferase-1 (DGAT1). As such, the methods of the invention find use in treating diseases, including without limitation, autoimmune diseases, which may be associated with TH17 polarized T cells; dysregulated induction of Treg cells; etc., for example EAE, MS, NMO, psoriasis, etc. in a subject.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

"Activity" of DGAT1 shall mean any signaling or binding function performed by that protein. DGAT1 is a multipass transmembrane protein that functions as a key metabolic enzyme. The encoded protein catalyzes the conversion of diacylglycerol and fatty acyl CoA to triacylglycerol. This enzyme can also transfer acyl CoA to retinol. Activity of this protein may be associated with obesity and other metabolic diseases.

The DGAT1 cDNA encodes a protein of 488 amino acids with 9 predicted transmembrane domains, a potential N-linked glycosylation site, and a putative tyrosine phosphorylation motif. There is high expression in the adrenal cortex, adrenal medulla, testes, and small intestine, with moderate expression in thyroid, stomach, heart, skeletal muscle, and liver.

Assays for DGAT1 enzymatic activity include, without limitation, measuring the conversion of diacylglycerol and fatty acyl CoA to triacylglycerol, for example with microsomes from cells expressing DGAT1, $^{14}$C-oleoyl CoA, diolein and a suitable buffer, where the labeled triacylglycerol is measured by any convenient method. For example, labeled TG can be extracted by chloroform-methanol, separated by TLC in hexane-diethylether-acetic acid, and quantified with an imager. Alternatively binding assays can be performed, for example by preparing microsomes from a DGAT1 expressing cell and incubating in the absence or presence of ligands. For competitive binding assays, labeled inhibitor and competing cold inhibitor are added. Bound inhibitor can be captured on 25 mM GF/C filter coated with 0.5% polyethyleneamine, washed, and quantified with a liquid scintillation analyzer. Bmax and Kd can be determined using one-site specific binding classical equation for nonlinear regression analysis. Competition data were analyzed with using sigmoidal dose-response (variable slope) classical equation for nonlinear regression analysis.

A number of small molecule DGAT1 inhibitors are known in the art, including without limitation: (1R,2R)-2-[[4'-[[Phenylamino)carbonyl]amino] [1,1'-biphenyl]-4-yl]carbonyl] cyclopentanecarboxylic acid (A922500); 2-((1,4-trans)-4-(4-(4-Amino-7,7-dimethyl-7H-pyrimido[4,5-b][1,4] oxazin-6-yl)-phenyl)cyclohexyl)acetic acid (T863); pyrimidinooxazinyl bicyclooctaneacetic acid (see Birch et al. (2009) J Med Chem 52: 1558-1568); 5-phenylthiazole containing biaryl analogs (see Kadam et al. (2013) Eur. J. Med. Chem. 65:337-347); cyclohexane carboxylic acid head group containing isoxazole and thiazole analogs (see Kandre et al. Eur J Med Chem. 2014 May 22; 79:203-15); quinoline carboxylic acid series (see Zhou et al. (2014) Bioorg Med Chem Lett. 24(7):1790-4); 2-((1r,4r)-4-(4-(6-carbamoyl-3, 5-dimethylpyrazin-2-yl) phenyl)cyclohexyl)acetic acid (AZD7687); etc.

Also see for DGAT1 inhibitors: Cheng et al. (2008) J Biol Chem 283(44), 29802-29811; Zhao et al. (2008) J Med Chem 51(3), 380-383; Kim et al. (2013) Biol Pharm Bull. 36(7):1167-73; Yeh et al. (2012) J Med Chem 55(4):1751-7; Enayetallah et al. (2011) PLoS One. 6(11):e27009; Cao et al. (2011) J. Biol. Chem. 286(48):41838-51; Yamamoto et al. (2011) Eur. J. Pharmacol. 650(2-3):663-72; Birch et al. (2010) Curr Opin Drug Discov Devel. 13(4):489-96; Matsuda et al. (2010) Expert Opin Ther Pat. 20(8):1097-102; each herein specifically incorporated by reference.

In some instances, the dosage of an agent that inhibits DGAT1, e.g. A922500 or other agents listed above, to be used in a human subject may be based on an effective dose of the agent as determined through pre-clinical testing, e.g., animal trials. For example, in some instances, a dosage, e.g., a dosage of A922500, found to be an effective dose in animal studies, e.g., mouse studies, may be converted to a human equivalent dose for use in humans. In one embodiment, based on studies in mice demonstrating effectiveness of dosages of A922500, for example ranging from 0.1 to 100 mg/kg/day, a human subject in need of treatment is correspondingly administered a dose ranging from 0.025 mg/kg/day, from 0.05 mg/kg/day, from 0.075 mg/kg/day, from 0.1 mg/kg/day, 0.25 mg/kg/day, 0.5 mg/kg/day, 0.75 mg/kg/day, 1 mg/kg/day, 2.5 mg/kg/day, 5 mg/kg/day, and up to 100 mg/kg/day, up to 75 mg/kg/day, up to 50 mg/kg/day, up to 25 mg/kg/day, up to 10 mg/kg/day. Dosage of other inhibitors may be administered at a dose that provides an effect equivalent to that of A922500.

Ranges intermediate to the above-recited ranges are also contemplated by the invention. For example, ranges having any one of these values as the upper or lower limits are also intended to be part of the invention, e.g., about 0.01 mg to about 100 mg, about 1 mg to about 10 mg, etc.

Conversion of an animal dose to human equivalent doses (HED) may, in some instances, be performed using the conversion table and/or algorithm provided by the U.S. Department of Health and Human Services, Food and Drug Administration, Center for Drug Evaluation and Research (CDER) in, e.g., *Guidance for Industry: Estimating the Maximum Safe Starting Dose in Initial Clinical Trials for Therapeutics in Adult Healthy Volunteers* (2005) Food and Drug Administration, 5600 Fishers Lane, Rockville, Md. 20857; (available at www(dot)fda(dot)gov/cder/guidance/index(dot)htm, the disclosure of which is incorporated herein by reference).

Anti-sense and RNAi inhibitors. As an alternative DGAT1 inhibitor, antisense reagents can be used in the methods of the invention. The antisense reagent may be antisense oligonucleotides (ODN), particularly synthetic ODN having chemical modifications from native nucleic acids, or nucleic acid constructs that express such antisense molecules as RNA. The antisense sequence is complementary to the targeted miRNA, and inhibits its expression. One or a combination of antisense molecules may be administered, where a combination may comprise multiple different sequences.

Antisense molecules may be produced by expression of all or a part of the target DGAT1 sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 25, usually not more than about 23-22 nucleotides in length, where the length is governed by efficiency of inhibition, specificity, including absence of cross-reactivity, and the like.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature that alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl, 2'-Fluoro, or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively. Anti-sense molecules of interest include antagomir RNAs, e.g. as described by Krutzfeldt et al., herein specifically incorporated by reference. Antagomirs are cholesterol-conjugated single-stranded RNA analogs. Antagomir RNAs may be synthesized using standard solid phase oligonucleotide synthesis protocols. The RNAs are conjugated to cholesterol, and may further have a phosphorothioate backbone at one or more positions.

Also of interest in certain embodiments are RNAi agents. By RNAi agent is meant an agent that modulates expression of DGAT1 mRNA by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, e.g., an sRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the sRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

In certain embodiments, instead of the RNAi agent being an interfering ribonucleic acid, e.g., an sRNA or shRNA as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

Where it is desirable to increase a target miRNA expression in a cell, an agent may be the targeted miRNA itself, including any of the modified oligonucleotides described above with respect to antisense, e.g. cholesterol conjugates, phosphorothioates linkages, and the like. Alternatively, a vector that expresses the targeted miRNA, including the pre-miRNA sequence relevant to the targeted organism, may be used.

Expression vectors may be used to introduce the target gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The expression cassette may employ an exogenous transcriptional initiation region, i.e. a promoter other than the native promoter. The promoter is functional in host cells, particularly host cells targeted by the cassette. The promoter may be introduced by recombinant methods in vitro, or as the result of homologous integration of the sequence by a suitable host cell. The promoter is operably linked to the miRNA sequence. Expression vectors conveniently will have restriction sites located near the promoter sequence to facilitate the insertion of miRNA sequences. The expression cassettes may be introduced into a variety of vectors. Promoters of interest may be inducible or constitutive, usually constitutive, and will provide for high levels of transcription in the vaccine recipient cells. The promoter may be active only in the recipient cell type, or may be broadly active in many different cell types. Many strong promoters for mammalian cells are known in the art, including the .beta.-actin promoter, SV40 early and late promoters, immunoglobulin promoter, human cytomegalovirus promoter, retroviral LTRs, etc. The promoters may or may not be associated with enhancers, where the enhancers may be naturally associated with the particular promoter or associated with a different promoter.

A termination region may be provided 3' to the coding region, where the termination region may be naturally associated with the variable region domain or may be derived from a different source. A wide variety of termination regions may be employed without adversely affecting expression.

The various manipulations may be carried out in vitro or may be performed in an appropriate host, e.g. *E. coli*. After each manipulation, the resulting construct may be cloned, the vector isolated, and the DNA screened or sequenced to ensure the correctness of the construct. The sequence may be screened by restriction analysis, sequencing, or the like.

"Antibody" shall include, by way of example, both naturally occurring and non-naturally occurring antibodies. Specifically, this term includes polyclonal and monoclonal antibodies, and fragments thereof. Furthermore, this term includes chimeric antibodies and wholly synthetic antibodies, and fragments thereof. Monoclonal antibodies are provided that bind to DGAT1 and block its activity.

"Comparable cell" shall mean a cell whose type is identical to that of another cell to which it is compared. Examples of comparable cells are cells from the same cell line.

"Inhibiting" the onset of a disorder shall mean either lessening the likelihood of the disorders onset, or preventing the onset of the disorder entirely. In the preferred embodiment, inhibiting the onset of a disorder means preventing its onset entirely. As used herein, onset may also refer to deterioration in a patient that has chronic/progressive disease, or relapse in a patient that has ongoing relapsing-remitting disease.

The methods of the invention may be specifically applied to individuals that have been diagnosed with an autoimmune disease, e.g. a chronic/progressive or relapsing-remitting disease such as MS, NMO, or EAE. Treatment is aimed at the treatment or prevention of relapses, which are an exacerbation of a pre-existing condition.

Active fragments of DGAT1 share a functional or binding property with full length DGAT1.

Epitopic fragments of DGAT1 bind to a monoclonal antibody that binds to full length DGAT1, including native or denatured forms of the protein.

"Specifically hybridize" to a nucleic acid shall mean, with respect to a first nucleic acid, that the first nucleic acid hybridizes to a second nucleic acid with greater affinity than to any other nucleic acid.

"Specifically inhibit" the expression of a protein shall mean to inhibit that protein's expression or activity (a) more than the expression or activity of any other protein, or (b) more than the expression or activity of all but 10 or fewer other proteins.

"Subject" or "patient" shall mean any animal, such as a human, non-human primate, mouse, rat, guinea pig or rabbit, etc.

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

"Treating" a disorder shall mean slowing, stopping or reversing the disorders progression. In the preferred embodiment, treating a disorder means reversing the disorders progression, ideally to the point of eliminating the disorder itself. As used herein, ameliorating a disorder and treating a disorder are equivalent.

As used herein, and unless otherwise specified, the terms "treat psoriasis," "treating psoriasis" and "treatment of psoriasis" refer to an action that occurs while a patient is suffering from psoriasis, which reduces the severity of psoriasis, or retards or slows the progression of the psoriasis, or achieving or maintaining a therapeutic objective. An "effective patient response" refers to any increase in the therapeutic benefit to the patient. An "effective patient psoriasis response" can be, for example, a 5%, 10%, 25%, 50%, or 100% decrease in the physical symptoms of psoriasis.

"Treatment of or "treating" psoriasis may mean achieving or maintaining a PGA score of 0/1 or a PASI 50, PASI 75, PASI 90, or PASI 100 response score for a period of time during or following treatment (e.g., for at least 2, 4, 6, 8, 10, 12, 14, 16, 18, 20, 22, 24, 26, 28, 30, 32, 34, 36, 38, 40, 42, 46, 48, 50, 52, 54, 56, 58 or 60 weeks or longer). "Treatment of or "treating" psoriasis may also mean achieving or maintaining a health-related quality of life (HRQOL) outcome. HRQOL outcomes include Dermatology Life Quality Index (DLQI), visual analog scales for Ps-related (VAS-Ps) and psoriatic arthritis-related (VAS-PsA) pain, Short Form 36 Health Survey Mental (MCS) and Physical (PCS) Component Summary scores, and Total Activity Impairment (TAI) scores.

"Treatment of or "treating" psoriasis may also mean achieving or maintaining a minimum clinically important difference (MCID) for any of the HRQOL outcomes provided herein, e.g., any one or combination of DLQI, VAS-Ps, VAS-PsA, MCS, PCS and TAI.

"Treatment of" or "treating" psoriasis may also mean achieving or maintaining a minimum clinically important difference (MCID) response rate for any of the HRQOL outcomes provided herein, e.g., any one or combination of DLQI, VAS-Ps, VAS-PsA, MCS, PCS and TAI. "Treatment of or "treating" psoriasis may also mean achieving or maintaining a clinically meaningful reduction in any of the HRQOL outcomes provided herein, e.g., any one or combination of DLQI, VAS-Ps, VAS-PsA, MCS, PCS and TAI.

"Treatment of or "treating" psoriasis may also mean achieving or maintaining a Nail Psoriasis Severity Index (NAPSI) score for a period of time during or following treatment (e.g., for at least 2, 4, 6, 8, 10, 12, 14, 16, 18, 20, 22, 24, 26, 28, 30, 32, 34, 36, 38, 40, 42, 46, 48, 50, 52, 54, 56, 58 or 60 weeks or longer).

"Treatment of" or "treating" psoriasis may also mean achieving or maintaining any of the outcomes provided herein in a certain percentage of a population of subjects (e.g., in at least about 10%, 15%, 20%, 25%, 30%, 35%, 40%, 45%, 50%, 55%, 60%, 65%, 70%, 75%, 80%, 85%, 90%, 95%, 99%, or 100% of a population of subjects).

The term "immune" response is the development of a beneficial humoral (antibody mediated) and/or a cellular (mediated by antigen-specific T cells or their secretion products) response directed against DGAT1 in a recipient patient. Such a response can be an active response induced by an "immunogen" that is capable of inducing an immunological response against itself on administration to a mammal, optionally in conjunction with an adjuvant.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

As used herein, the term "dose amount" refers to the quantity, e.g., milligrams (mg), of the substance which is administered to the subject. In one embodiment, the dose amount is a fixed dose, e.g., is not dependent on the weight of the subject to which the substance is administered. In another embodiment, the dose amount is not a fixed dose, e.g., is dependent on the weight of the subject to which the substance is administered, or for a topical therapy a dose may be related to the surface area that is treated, e.g. dose/m$^2$ of skin.

As used herein, the term "periodicity" as it relates to the administration of a substance refers to a (regular) recurring cycle of administering the substance to a subject. In one embodiment, the recurring cycle of administration of the substance to the subject achieves a therapeutic objective. The periodicity of administration of the substance may be about once a week, once every other week, about once every three weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks, about once every 21 weeks, about once every 22 weeks, about once every 23 weeks, about once every 24 weeks, about once every 5-10 days, about once every 10-20 days, about once every 10-50 days, about once every 10-100 days, about once every 10-200 days, about once every 25-35 days, about once every 20-50 days, about once every 20-100 days, about once every 20-200 days, about once every 30-50 days, about once every 30-90 days, about once every 30-100 days, about once every 30-200 days, about once every 50-150 days, about once every 50-200 days, about once every 60-180 days, or about once every 80-100 days. Periodicities intermediate to the above-recited times are also contemplated by the invention. Ranges intermediate to the above-recited ranges are also contemplated by the invention. For example, ranges having any one of these values as the upper or lower limits are also intended to be part of the invention, e.g., about 110 days to about 170 days, about 160 days to about 220 days, etc.

The "duration of a periodicity" refers to a time over which the recurring cycle of administration occurs. For example, a duration of the periodicity of administration of a substance may be may be up to about 4 weeks, up to about 8 weeks, up to about 12 weeks, up to about 16 weeks or more, up to about 20 weeks, up to about 24 weeks, up to about 28 week, up to about 32 weeks or more, during which the periodicity of administration is about once every week. For example, a duration of the periodicity may be about 6 weeks during which the periodicity of administration is about once every 4 weeks, e.g., the substance is administered at week zero and at week four.

In one embodiment, the duration of periodicity is for a length of time necessary or required to achieve a therapeutic objective, e.g., treatment, maintenance of treatment, etc. e.g., maintain a PASI 50, PASI 75, PASI 90, PASI 100 score or PGA of 0 or 1 score. Durations of a periodicity intermediate to the above-recited times are also contemplated by the invention.

Methods of the Invention

The present invention provides methods for treating autoimmune disease, including without limitation autoimmune diseases associated with TH17 polarized T cells, with dysregulated regulatory T cells, etc. Diseases of interest may include multiple sclerosis (MS), systemic lupus erythematosus (SLE), inflammatory bowel disease (IBD), rheumatoid arthritis (RA), psoriasis, type I diabetes, and Crohn's disease. For example, see Waite and Skokos (2012) Int. J. Inflammation, article ID 819467, herein specifically incorporated by reference.

Conditions of particular interest for treatment with the methods of the invention include inflammatory demyelinating diseases, such multiple sclerosis; NMO, EAE, etc. These methods comprise administering to the subject having an autoimmune condition, e.g. a demyelinating condition; an effective amount of an inhibitor of DGAT1, where the dose is effective to decrease symptoms of the disease, including, for example, a decrease in the DGAT1 activity of CNS infiltrating lymphocytes; a decrease in the number of inflammatory foci; a decrease in the number of CNS infiltrating lymphocytes, and the like.

In some embodiments, a method is provided for inhibiting autoimmune diseases in a subject, the method comprising administering to the subject a prophylactically effective amount of a nucleic acid that specifically reduces levels of DGAT1, e.g. an anti-sense oligonucleotide, siRNA, and the like.

In other embodiments, a method is provided for inhibiting inflammatory demyelinating disease in a subject, the method comprising administering to the subject a therapeutically effective amount of an anti-DGAT1 antibody or antigen-binding portion thereof. In other embodiments the condition for treatment is psoriasis.

In some such embodiments, the method comprising administering to said subject a small molecule inhibitor of DGAT1. In some such embodiments the small molecule is one or more, e.g. a cocktail of agents with differing activity, A922500; T863; LCQ-908, pyrimidinooxazinyl bicyclooctaneacetic acid; 5-phenylthiazole containing biaryl analogs; cyclohexane carboxylic acid head group containing isoxazole and thiazole analogs; quinoline carboxylic acid series; 2-((1r,4r)-4-(4-(6-carbamoyl-3,5-dimethylpyrazin-2-yl)phenyl)cyclohexyl)acetic acid (AZD7687); etc. See, for example, Birch et al. (2010) Curr Opin Drug Discov Devel. 2010 July; 13(4):489-96; and DeVita et al. (2013) J. Med. Chem 56(24):9820-5; each herein specifically incorporated by reference for teachings relating to the use of DGAT1 inhibitors.

Determining a therapeutically or prophylactically effective amount of the DGAT1 inhibitor compositions can be done based on animal data using routine computational methods. In one embodiment, the therapeutically or prophylactically effective amount contains between about 0.001 mg and about 1 g of inhibitor, as applicable.

Exemplary dose amounts, e.g., fixed dose amounts, for use treating an adult human by the methods of the invention include, about 0.01 mg, about 0.05 mg, about 0.1 mg, about 0.5 mg, about 1 mg, about 5 mg, about 10 mg, about 50 mg, about 100 mg, about 500 mg, or more.

Ranges intermediate to the above-recited ranges are also contemplated by the invention. For example, ranges having any one of these values as the upper or lower limits are also intended to be part of the invention, e.g., about 0.01 mg to about 100 mg, about 1 mg to about 10 mg, etc.

In this invention, administering the instant compositions can be effected or performed using any of the various methods and delivery systems known to those skilled in the art. The administering can be performed, for example, intravenously, orally, via implant, transmucosally, transdermally, intramuscularly, intrathecally, and subcutaneously. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol, and sucrose) and polymers (e.g., cyclodextrin, polycaprylactones and PLGA's). Implantable systems include rods and discs, and can contain excipients such as PLGA and polycaprylactone. DGAT1 or nucleic acids of the invention can also be administered attached to particles using a gene gun.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, xanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and Jun. 2, 2005 antioxidants (e.g., parabens, vitamins E and C, and ascorbic acid), anti-caking agents, coating agents, and chelating agents (e.g., EDTA).

Conditions for Analysis and Therapy

The compositions and methods of the invention find use in combination with a variety of demyelinating autoimmune conditions, including chronic/progressive and relapsing demyelinating autoimmune diseases. Generally patients for the methods of the present invention are diagnosed as having an autoimmune condition, e.g. a relapsing-remitting autoimmune condition, prior to treatment. The inhibition of DGAT1 decreases the severity or incidence of relapses in such patients.

Multiple sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

Clinical data alone may be sufficient for a diagnosis of MS. If an individual has suffered two separate episodes of neurologic symptoms characteristic of MS, and the individual also has consistent abnormalities on physical examination, a diagnosis of MS can be made with no further testing. Magnetic resonance imaging (MRI) of the brain and spine is often used during the diagnostic process. MRI shows areas of demyelination (lesions) as bright spots on the image. A substance, called Gadolinium, can be injected into the spinal column to highlight active plaques and, by elimination, demonstrate the existence of historical lesions not associated with clinical symptoms. This can provide the evidence of chronic disease needed for a definitive diagnosis of MS. Testing of cerebrospinal fluid (CSF) can provide evidence of chronic inflammation of the central nervous system. The CSF is tested for oligoclonal bands, which are immunoglobulins found in 85% to 95% of people with definite MS. Combined with MRI and clinical data, the presence of oligoclonal bands can help make a definite diagnosis of MS. Lumbar puncture is the procedure used to collect a sample of CSF.

The brain of a person with MS often responds less actively to stimulation of the optic nerve and sensory nerves. These brain responses can be examined using visual evoked potentials (VEPs) and somatosensory evoked potentials (SEPs). Decreased activity on either test can reveal demyelination which may be otherwise asymptomatic. Along with other data, these exams can help find the widespread nerve involvement required for a definite diagnosis of MS.

In 1996 the United States National Multiple Sclerosis Society standardized the following four subtype definitions (see Lublin and Reingold (1996) Neurology 46(4):907-11, herein specifically incorporated by reference) as relapsing-remitting; secondary progressive; primary progressive; progressive relapsing. The methods of the invention find particular use in the treatment of ongoing disease, and particularly in treating relapsing forms.

Relapsing-remitting describes the initial course of 85% to 90% of individuals with MS. This subtype is characterized by unpredictable attacks (relapses) followed by periods of months to years of relative quiet (remission) with no new signs of disease activity. Deficits suffered during the attacks may either resolve or may be permanent. When deficits always resolve between attacks, this is referred to as "benign" MS.

Secondary progressive describes around 80% of those with initial relapsing-remitting MS, who then begin to have neurologic decline between their acute attacks without any definite periods of remission. This decline may include new neurologic symptoms, worsening cognitive function, or other deficits. Secondary progressive is the most common type of MS and causes the greatest amount of disability.

Primary progressive describes the approximately 10% of individuals who never have remission after their initial MS symptoms. Decline occurs continuously without clear attacks. The primary progressive subtype tends to affect people who are older at disease onset.

Progressive relapsing describes those individuals who, from the onset of their MS, have a steady neurologic decline but also suffer superimposed attacks; and is the least common of all subtypes.

Treatments for MS include interferon β (Avonex, Betaseron, Rebif), Copaxone (Glatiramer acetate), and anti-VLA4 (Tysabri, natalizumab), which reduce relapse rate and to date have only exhibited a modest impact on disease progression. MS is also treated with immunosuppressive agents including methylprednisolone, other steroids, methotrexate, cladribine and cyclophosphamide. Many biological agents, such as anti-IFNgamma antibody, CTLA4-Ig (Abetacept), anti-CD20 (Rituxan), and other anti-cytokine agents are in clinical development for MS.

Peripheral neuropathies may also have a relapsing remitting course, and may include Miller Fisher syndrome; chronic inflammatory demyelinating polyneuropathy (CIDP) with its subtypes classical CIDP, CIDP with diabetes, CIDP/monoclonal gammopathy of undetermined significance (MGUS), sensory CIDP, multifocal motor neuropathy (MMN), multifocal acquired demyelinating sensory and motor neuropathy or Lewis-Sumner syndrome, multifocal acquired sensory and motor neuropathy, and distal acquired demyelinating sensory neuropathy; IgM monoclonal gammopathies with its subtypes Waldenstrom's macroglobulinemia, myelin-associated glycoprotein-associated gammopathy, polyneuropathy, organomegaly, endocrinopathy, M-protein, skin changes syndrome, mixed cryoglobulinemia, gait ataxia, late-onset polyneuropathy syndrome, and MGUS.

Chronic plaque psoriasis (also referred to as psoriasis vulgaris) is the most common form of psoriasis. Chronic plaque psoriasis is characterized by raised reddened patches of skin, ranging from coin-sized to much larger. In chronic plaque psoriasis, the plaques may be single or multiple, they may vary in size from a few millimeters to several centimeters. The plaques are usually red with a scaly surface, and reflect light when gently scratched, creating a "silvery" effect. Lesions (which are often symmetrical) from chronic plaque psoriasis occur all over body, but with predilection for extensor surfaces, including the knees, elbows, lumbosacral regions, scalp, and nails. Occasionally chronic plaque psoriasis can occur on the penis, vulva and flexures, but scaling is usually absent. Diagnosis of patients with chronic plaque psoriasis is usually based on the clinical features described above. In particular, the distribution, color and typical silvery scaling of the lesion in chronic plaque psoriasis are characteristic of chronic plaque psoriasis.

Guttate psoriasis refers to a form of psoriasis with characteristic water drop shaped scaly plaques. Flares of guttate psoriasis generally follow an infection, most notably a streptococcal throat infection. Diagnosis of guttate psoriasis is usually based on the appearance of the skin, and the fact that there is often a history of recent sore throat.

Inverse psoriasis is a form of psoriasis in which the patient has smooth, usually moist areas of skin that are red and inflamed, which is unlike the scaling associated with plaque psoriasis. Inverse psoriasis is also referred to as intertiginous psoriasis or flexural psoriasis. Inverse psoriasis occurs mostly in the armpits, groin, under the breasts and in other skin folds around the genitals and buttocks, and, as a result of the locations of presentation, rubbing and sweating can irritate the affected areas.

Pustular psoriasis, also referred to as palmar plantar psoriasis, is a form of psoriasis that causes pus-filled blisters that vary in size and location, but often occur on the hands and feet. The blisters may be localized, or spread over large areas of the body. Pustular psoriasis can be both tender and painful, can cause fevers.

Erythrodermic psoriasis is a particularly inflammatory form of psoriasis that often affects most of the body surface. It may occur in association with von Zumbusch pustular psoriasis. It is a rare type of psoriasis, occurring once or more during the lifetime of 3 percent of people who have psoriasis. It generally appears on people who have unstable plaque psoriasis. Widespread, fiery redness and exfoliation of the skin characterize this form. Severe itching and pain often accompanies it. Erythrodermic psoriasis causes protein and fluid loss that can lead to severe illness. Edema (swelling from fluid retention), especially around the ankles, may develop, along with infection. Erythrodermic psoriasis also can bring on pneumonia and congestive heart failure. People with severe cases often require hospitalization. Erythrodermic psoriasis can occur abruptly at the first signs of psoriasis or it can come on gradually in people with plaque psoriasis. Combination treatments are frequently required, for example topical products and one or two systemic medications.

Agents

An inhibitory agent may inhibit the activity of DGAT1 by a variety of different mechanisms. In certain embodiments, the inhibitory agent is one that binds to the protein DGAT1 and, in doing so, inhibits its activity. In other embodiments, the inhibitory agent prevents expression or secretion of DGAT1.

The inhibitory agent may act on DGAT1 mRNA to inhibit the activity of the target DGAT1 by reducing the amount of DGAT1 RNA present in the targeted cells, where the target cell may be present in vitro or in vivo. By "reducing the amount of" is meant that the level or quantity of the target DGAT1 in the target cell is reduced by at least about 2-fold, usually by at least about 5-fold, e.g., 10-fold, 15-fold, 20-fold, 50-fold, 100-fold or more, as compared to a control, i.e., an identical target cell not treated according to the subject methods.

In another embodiment, the DGAT1 inhibitor is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The term includes monoclonal antibodies, multispecific antibodies (antibodies that include more than one domain specificity), human antibody, humanized antibody, and antibody fragments with the desired biological activity.

The methods of the invention also provide for combination therapy, where the combination can provide for additive or synergistic benefits. Combinations of agents can be obtained with a second agent selected from one or more of the general classes of drugs commonly used in the treatment of the disease of interest, for example including corticosteroids and disease modifying drugs, antigen-specific agents, etc. Corticosteroids have a short onset of action, but many disease modifying drugs take several weeks or months to demonstrate a clinical effect. These agents include methotrexate, leflunomide (Arava™) etanercept (Enbrel™), infliximab (Remicade™), adalimumab (Humira™), anakinra (Kineret™) rituximab (Rituxan™), CTLA4-Ig (abatacept), antimalarials, gold salts, sulfasalazine, d-penicillamine, cyclosporin A, cyclophosphamide azathioprine; and the like. Corticosteroids, e.g. prednisone, methylpredisone, prednisolone, solumedrol, etc. have both anti-inflammatory and immunoregulatory activity. They can be given systemically or can be injected locally. Corticosteroids are useful in early disease as temporary adjunctive therapy while waiting for disease modifying agents to exert their effects. Corticosteroids are also useful as chronic adjunctive therapy in patients with severe disease.

In some embodiments of the invention the therapeutic agent is a beta-interferon, including without limitation the currently approved drugs AVONEX™ (IFNβ 1A), BETASERON™ (IFN-β1B); EXTAVIA™ (IFN-β1B), REBIF™ (IFNβ1A), and bioequivalents and derivatives, e.g. pegylated derivatives, thereof. Conditions that can be treated with β-interferons include MS, EAE, etc. Such diseases can also be treated with glatiramer acetate (Copaxone).

In some embodiments of the invention the therapeutic agent is a cytokine or an antagonist, agonist, mimetic, bioequivalent, or derivative thereof. Cytokines of interest include, without limitation, IL-1β; IL-2; IL-4; IL-5; IL-6; IL-7; IL-8; IL-10; IL-11; IL-12; IL-13; IL-15; IL-17 (including IL-17A, B, C, D, E, F separately and in combination, such as IL-17A/F); IL-18; IL-20; IL-21; IL-23; and IL29.

Antagonists of interleukins which can be soluble receptors, antibodies, small molecule drugs, etc. include, without limitation, anti-IL-1, e.g. canakinumab, anakinra, rilonacept, AMG108, XOMA052; anti-IL-4, AMG317; anti-IL-5, mepolizumab, reslizumab, SCH55700, MEDI-563 (receptor); anti-IL6, siltuximab, tocilizumab (receptor), CNTO 136; anti-IL-8, ABX-IL8; anti-IL-9, MEDI-528; anti-IL-12 and IL-23, ustekinumab, briakinumab; anti-IL-13, CAT-354, QAX576; anti-IL-15, AMG 714; anti-IL-17, AIN457, LY2439821, NI-1401; anti-IL-18, GSK1070806; anti-IL-20, NNC109-0012; anti-IL-22, fezakinumab; anti-IL-23, LY2525623. STA-5326 (also called apilimod) is a small molecule inhibitor of IL-12/23 function. LY2439821 and secukinumab (AIN457) are examples of anti-IL-17 monoclonal antibodies.

Antagonists of cytokines include antagonists of IFNα (anti-IFNα); IFNβ (anti-IFNβ); IFNγ (anti-IFNγ); G-CSF (anti-G-CSF); GM-CSF (anti-GM-CSF); Groα (anti-Groα); etc. Agonists of TNFα (anti TNFα), e.g. Enbrel (etanercept), Arcalyst (rilonacept), Amevive (alefacept), find use, for example in the treatment of rheumatic diseases. As used herein, rheumatic diseases can include Ankylosing Spondylitis, Gout, Rheumatoid Arthritis, acute and subacute Bursitis, Kawasaki Syndrome, Relapsing Polychondritis, Bursitis and Tendinitis, Juvenive Idiopathic Arthritis (Juvenile Rheumatoid Arthritis), Sjogren's Syndrome, Cryopyrin-associated Periodic Syndromes, Osteoarthritis, Systemic Sclerosis, Dermatomyositis, Polymyalgia Rheumaticia, Systemic Lupus Erythematous, Epicondylitis, Polymyositis, acute non-specific Tenosynovitis, Fibromyalgia, Psoriatic Arthritis and Vasculitis. Therapies known for rheumatic diseases also include Abatacept (Orencia); Adalimumab (Humira); Anakinra (Kineret); Aspirin (Ecotrin); Auranofin (Ridura); Aurothioglucose (Solganal); Azathioprine (Imuran); Celecoxib (Celebrex); Cyclosporin (Neoral); Etanercept (Enbrel); Gold sodium thiomalate (Myochrysine); Hydroxychloroquine Sulfate (Plaquenil); Infliximab (Remicade); Intravenous Immunoglobulin (Gammagard S/D); Leflunomide (Arava); Methylprednisolone acetate (Depo-Medrol); Methotrexate (Rheumatrex, Trexall); Penicillamine (Cuprimine); Prednisolone (Prednisone (Corticosteroids); Rilonacept (Arcalyst); Rituximab (Rituxan); Sulfasalazine (Azulfidine (Azulfidine EN-Tabs); Triamcinolone acetonide (Kenalog); Triamcinolone diacetate (Aristospan); Diclofenac (Voltaren (Cataflam (Arthrotec (combined with misoprostol)); Diflunisal (Dolobid); Etodolac (Lodine (Lodine XL); Fenoprofen (Nalfon (Nalfon 200); Flurbiprofen (Ansaid); Ibuprofen (Motrin, Tab-Profen, Vicoprofen, combined with hydrocodone) (Combunox, combined with oxycodone); Ibuprofen (Children's Advil); Indomethacin (Indocin, Indocin SR, Indo-Lemmon); Ketoprofen (Oruvail, Orudis); Meloxicam (Mobic); Nabumetone (Relafen); Naproxen (Naprosyn, Anaprox, Anaprox DS, EC-Naprosyn, Naprelan); Oxaprozin (Daypro); Piroxicam (Feldene); Sulindac (Clinoril); Tolmetin (Tolectin, Tolectin DS, Tolectin 600).

Agents that find use in the treatment of chronic hepatitis include, for example, ALFERON N™ INJECTION (IFN-αN3); INFERGEN™ (IFN-αCON-1); INTRON A™ (IFN-α2B); PEGASYS™ (PEG IFN-α2A); PEGINTERFERON™ (PEGIFN-α2A; RIBAVIRIN); PEGINTRON™ (PEGIFN-α2B); ROFERON A™ (IFN-α2A).

Agents that have been found useful in treating inflammatory diseases also include statins, e.g. pravastatin, simvastatin, lovastatin, fluvastatin, atorvistatin, pitavastatin, rosuvastatin, etc.

Monoclonal antibodies in use include, without limitation, ACTEMRA™ (tocilizumab); ARZERRA™ (ofatumumab); BEXXAR™ (tositumomab; $^{131}$I tositumomab); CAMPATH™ (alemtuzumab); CIMZIA™ (certolizumab pegol); HUMIRA™ (adalimumab); ILARIS™ (canakinumab); PROLIA™ (denosumab); REMICADE™ (infliximab); RITUXAN™ (rituximab); SIMPONI™ (golimumab); SIMULECT™ (basiliximab); STELARA™ (ustekinumab); TYSABRI™ (natalizumab); XGEVA™ (denosumab); XOLAIR™ (omalizumab); ZENAPAX™ (daclizumab). Monoclonal antibodies specific for amyloid include LY2062430 (solanezumab), PF-04360365, MABT5102A, bapineuzumab, gantenerumab.

Other therapeutic agents of interest include lenalidomide (Revlimid); fingolimod (Gilenya); teriflunomide; cladribine; and BG-12 (Panaclar, BG-00012, FAG-201); JAK inhibitors and Syk inhibitors, which include without limitation the JAK-3 inhibitor tasocitinib (CP-690,550); Syk inhibitor fostamatinib (R788) etc.

EXPERIMENTAL

Example 1

CD4 T lymphocytes have key roles in the pathology of multiple sclerosis (MS), but the mechanisms that govern T cell effector functions within the central nervous system (CNS) are poorly understood. To define potential novel regulators of pathogenic CNS inflammation, we performed transcriptional profiling of memory phenotype CD4 T cells FACS-sorted from CNS and lymphoid tissues of mice with experimental autoimmune encephalomyelitis (EAE), a model of human MS. We found that mRNA for diacylglycerol O-acyltransferase-1 (DGAT1), a lipid-synthesizing enzyme, was highly upregulated by CNS-infiltrating memory CD4 T cells from mice with EAE by induced by myelin oligodendrocyte glycoprotein (MOG) peptide amino acids 35-35 ($MOG_{35-55}$).

Mice deficient in DGAT1 developed less severe clinical symptoms and had significantly fewer mononuclear cell infiltrates within the CNS than their wild-type (WT) counterparts, consistent with a critical role for the enzyme in autoimmune demyelinating disease. DGAT1 deficiency ameliorates Th17-mediated EAE in an adoptive transfer model of disease. Naive C57BL/6 WT mice were injected with $MOG_{35-55}$-reactive WT or DGAT1 KO CD4 T cells differentiated in vitro under Th1 (top) or Th17 (bottom) polarization conditions. Data were pooled from two independent experiments (n=3-5 recipient mice/group for each experiment), and are presented as mean clinical score ±SEM. *$P<0.05$ by Mann-Whitney U test.

TABLE 1

Summary of clinical disease in mice induced to develop EAE by adoptive transfer[a]

| Donor cell genotype/ polarization | Disease incidence | Mean maximal score (SEM) | Mean day of onset (SEM)[b] |
|---|---|---|---|
| WT/Th1 | 8/8 (100%) | 2.8 (0.2) | 8.5 (0.3) |
| DGAT1 KO/Th1 | 7/7 (100%) | 2.1 (0.1)[c] | 10.0 (0.3)[d] |
| WT/Th17 | 8/8 (100%) | 3.1 (0.1) | 8.5 (0.3) |
| DGAT1 KO/Th17 | 6/8 (75%) | 1.5 (0.3)[e] | 11.2 (1.0)[f] |

[a]Data are pooled from two independent experiments with each experiment consisting of 3-5 mice per group.
[b]Determined only for animals that developed EAE.
[c]$p < 0.05$; and
[e]$p < 0.001$ (compared to WT/Th1 and WT/Th17, respectively) by Mann-Whitney U test.
[d,f]$p < 0.01$ (compared to WT/Th1 and WT/Th17, respectively) by Student's t test.

In addition, administration of a selective DGAT1 inhibitor attenuated $MOG_{35-55}$-induced EAE. C57BL/6 mice (8 weeks old) were induced to develop EAE by active immunization with $MOG_{35-55}$/CFA. Twelve days after disease induction (indicated by the arrow), mice were administered vehicle (10% Captisol) or 10 mg/kg DGAT1 inhibitor A922500 once daily via s.c. injection and followed for clinical disease (n=10/group). Clinical data are presented as the mean score ±SEM. The scoring system is as follows: 0, normal or healthy; 1, limp tail; 2, hindlimb weakness; 3, hindlimb paralysis; 4, hindlimb and forelimb paralysis. *P<0.05 (days 14-30) by Mann-Whitney U test.

C57BL/6 and DGAT1 KO mice (8-10 weeks old) were induced to develop EAE by active immunization with $MOG_{35-55}$/CFA and followed daily for clinical symptoms (n=25/group for days 0-17 pi; and n=20/group for days 18-30 pi). *P<0.05 for days 12-30 p.i., by Mann-Whitney U test. The scoring system for our EAE studies is as follows: 0, normal or healthy; 1, limp tail; 2, hindlimb weakness; 3, hindlimb paralysis; 4, hindlimb and forelimb paralysis. Data are presented as mean clinical score ±SEM. Representative of 2 independent experiments. (B) Histological changes in CNS leptomeninges and parenchyma (n=10/group) were evaluated in a blinded fashion (Total=Meninges+Parenchyma). Bars represent mean±SEM. *P<0.05 by Student's t test.

Collectively, these results demonstrate the ability of CNS-specific CD4 T cell expression profiling to define novel factors of therapeutic relevance in EAE. Through the use of genetic and pharmacologic approaches, we identify DGAT1 as a regulator of immune pathology and T cell effector function during EAE. DGAT1-targeted therapies represent a novel treatment strategy in MS.

Example 2

DGAT1 Inhibits Retinoic Acid-Dependent Regulatory T Cell Generation and Mediates Autoimmune Encephalomyelitis An imbalance of regulatory versus effector CD4+ T cells can contribute to multiple sclerosis (MS), but mechanisms that govern CD4+ T cell functions within the central nervous system (CNS) remain poorly defined. Transcriptional profiling identified expression of Dgat1, a gene encoding diacylglycerol O-acyltransferase-1, by CNS-infiltrating CD4+ T cells from mice with experimental autoimmune encephalomyelitis (EAE). A selective DGAT1 inhibitor attenuated EAE, and DGAT1–/– in vitro-polarized Th17 effectors were inefficient at EAE induction. Retinoic acid (RA) induces T regulatory cells (Tregs), and DGAT1 can sequester RA in retinyl ester form. Provision of the RA precursor retinol during T cell activation in vitro enhanced Treg induction from DGAT1–/– but not wild type (WT) naive T cell precursors; however, addition of a pharmacologic DGAT1 inhibitor or a synthetic RA receptor agonist circumvented this retinol-dependent WT Treg induction defect. Our results identify DGAT1 as an enzyme regulator of RA-dependent Treg formation and an MS therapeutic target.

To identify potential novel mediators of autoimmune CNS inflammation, we performed whole-genome expression analysis of memCD4Ts isolated from tissues of mice with EAE induced by active immunization with myelin oligodendrocyte glycoprotein (MOG) peptide amino acids 35-35 ($MOG_{35-55}$). We found that CNS-infiltrating memCD4Ts from mice with acute clinical EAE expressed high levels of mRNA for diacylglycerol O-acyltransferase-1 (Dgat1), an enzyme that catalyzes the final step of triglyceride synthesis. DGAT1 is expressed at the protein level by adipocytes and macrophages, but little is known about roles for DGAT1 in T cells specifically or in the immune system in general. Here, we evaluated roles for DGAT1 in clinical disease and T cell function during EAE.

Results

Memory CD4+ T Cell Transcriptional Profiling Identifies Key Effector Molecules in EAE.

We induced EAE in C57BL/6 mice by active immunization with $MOG_{35-55}$ emulsified in complete Freund's adjuvant (CFA). We performed transcriptional profiling of FACS-sorted memCD4Ts ($CD44^{hi}CD45RB^{lo}CD25-$) from CNS and draining lymph node (dLN) tissues (i.e., inguinal LN) of mice with acute clinical EAE (13-17 days post-immunization, or p.i.). For comparison, we also sorted naive ($CD44^{lo}CD45RB^{hi}CD25-$) and memCD4Ts from peripheral lymph nodes (PLNs) of naive, healthy mice. Sorted populations were >98% pure, as determined by flow cytometry.

To identify genes selectively or differentially expressed by effector T cells within the target tissue (versus genes upregulated in the periphery as a consequence of MOG/CFA immunization), we compared expression profiles of CNS memCD4Ts and EAE dLN memCD4Ts. Analysis of the gene expression-profiling data yielded several confirmatory findings. First, when compared with memCD4Ts from EAE dLN (or memCD4Ts from PLN of naive mice), CNS memCD4Ts had much higher expression of several EAE- and MS-associated genes, such as interferon-gamma (Ifng) and Fas ligand (Fasl). CNS memCD4Ts had relatively lower expression of other key molecules. Examples include: Cd27, a costimulatory molecule that represses expression of IL-17A and CCR6, and the trafficking receptors Ccr7 and L-selectin (Sell), consistent with reports that T cells downregulate these receptors upon entry into extra-lymphoid tissues. CNS memCD4Ts also had upregulated genes for several transcription factors associated with pathogenic T cell activity. Among the most highly differentially expressed transcription factor family members within the CNS memCD4T dataset were: nuclear receptor subfamily 4, group A, member 2 (Nr4a2), which promotes pro-inflammatory cytokine production by T cells during EAE and MS; and cAMP responsive element modulator (Crem), which has been linked with autoreactive T helper 17 (Th17) cell differentiation. Collectively, the gene signatures of CNS-infiltrating memCD4Ts are consistent with expected results and published observations, suggesting that a memCD4T-focused profiling approach could potentially identify previously unknown regulators of EAE and MS pathology (FIG. 1, FIG. 2a and Table 3).

CNS-Infiltrating Memory Phenotype CD4+ T Cells Express Dgat1.

Further examination of the microarray datasets revealed that, compared to memory and naive CD4+ T cells from PLNs (including memCD4Ts from the dLN tissues of mice with EAE), CNS memCD4Ts significantly upregulated several potentially interesting molecules. The gene for diacylglycerol O-acyltransferase-1 (Dgat1)—an enzyme that catalyzes triglyceride (TG) formation in mammalian cells—was included among transcripts that were highly and selectively expressed by CNS memCD4Ts (FIG. 2a, FIG. 2b and Table 3). In fact, the relative expression level of Dgat1 (i.e., fold change difference in CNS memCD4Ts versus EAE dLN memCD4Ts) exceeded Tnf, Stat3, and several other well-defined mediators of pathology and T cell effector functions in EAE/MS (Table 3), consistent with robust expression. DGAT1 and DGAT2 both catalyze the final step in TG synthesis, but Dgat2 was not significantly upregulated by CNS memCD4Ts, an observation that we confirmed by real-time reverse transcriptase quantitative PCR (RT-QPCR) analysis (FIG. 2b, FIG. 2c). A query of public microarray datasets (e.g., the Immunological Genome Project and BioGPS) also reveals that, consistent with our microarray and RT-QPCR results, naive and memCD4Ts from peripheral lymphoid tissues do not contain significant Dgat1 message; and that Dgat1 is not expressed in normal brain tissues or cells (e.g., FACS-sorted microglia). Thus, high-level expression of Dgat1 transcripts by sorted CNS memCD4Ts is likely not caused by contamination from other cell types.

Figure 2:
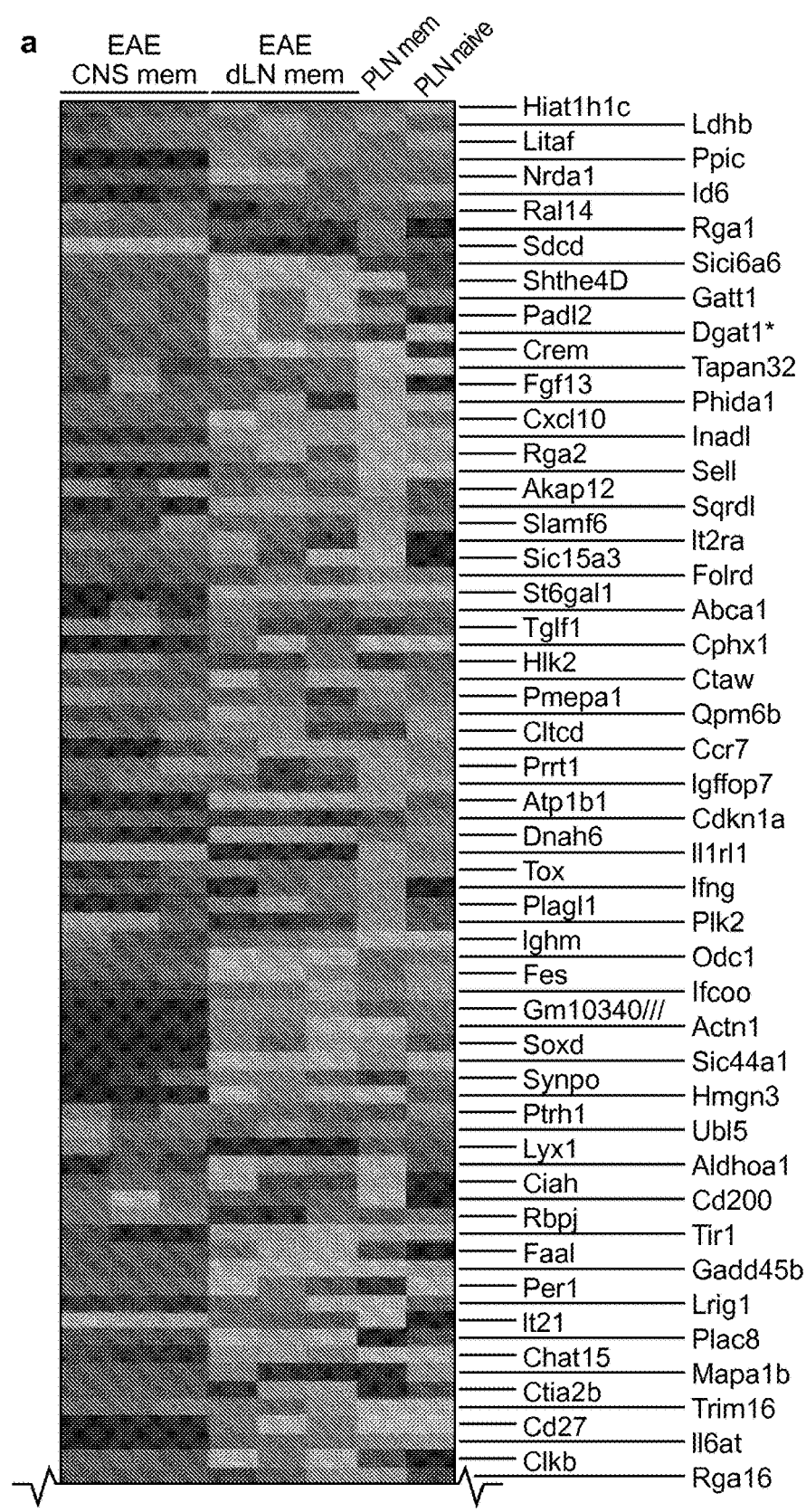
FIG. 2. CNS-infiltrating memory phenotype CD4+ T cells upregulate Dgat1. Differentially expressed genes identified in FIG. 1 were selected for further analysis. (a) Heat map display of genes with at least a fourfold difference in expression in CNS memCD4T versus EAE dLN memCD4T. Each row represents an individual gene, and each column represents an individual experiment/tissue. Red indicates upregulated genes, while downregulated genes are in blue. The red asterisk highlights the position of Dgat1. (b) Heat map display of gene expression data for Dgat1, Dgat2 and Lrat. Mean raw expression values (±SEM) for CNS memCD4Ts are as follows: Dgat1, 8746 (2495); Dgat2, 215 (13); and Lrat, 16 (0.2). Values for EAE dLN memCD4s are: Dgat1, 1101 (247); Dgat2, 151 (25); Lrat, 17 (0.8). (c) Scatterplots depict RT-QPCR analysis of Dgat1 (left) and Dgat2 (right) mRNA expression (normalized to β-actin levels) by naive and memory phenotype CD4+ T cells. Each point represents a biological replicate, and the bars represent mean±SEM. *$P<0.05$ by ANOVA. AU, arbitrary units. PLN, peripheral LN.
Figure 2:
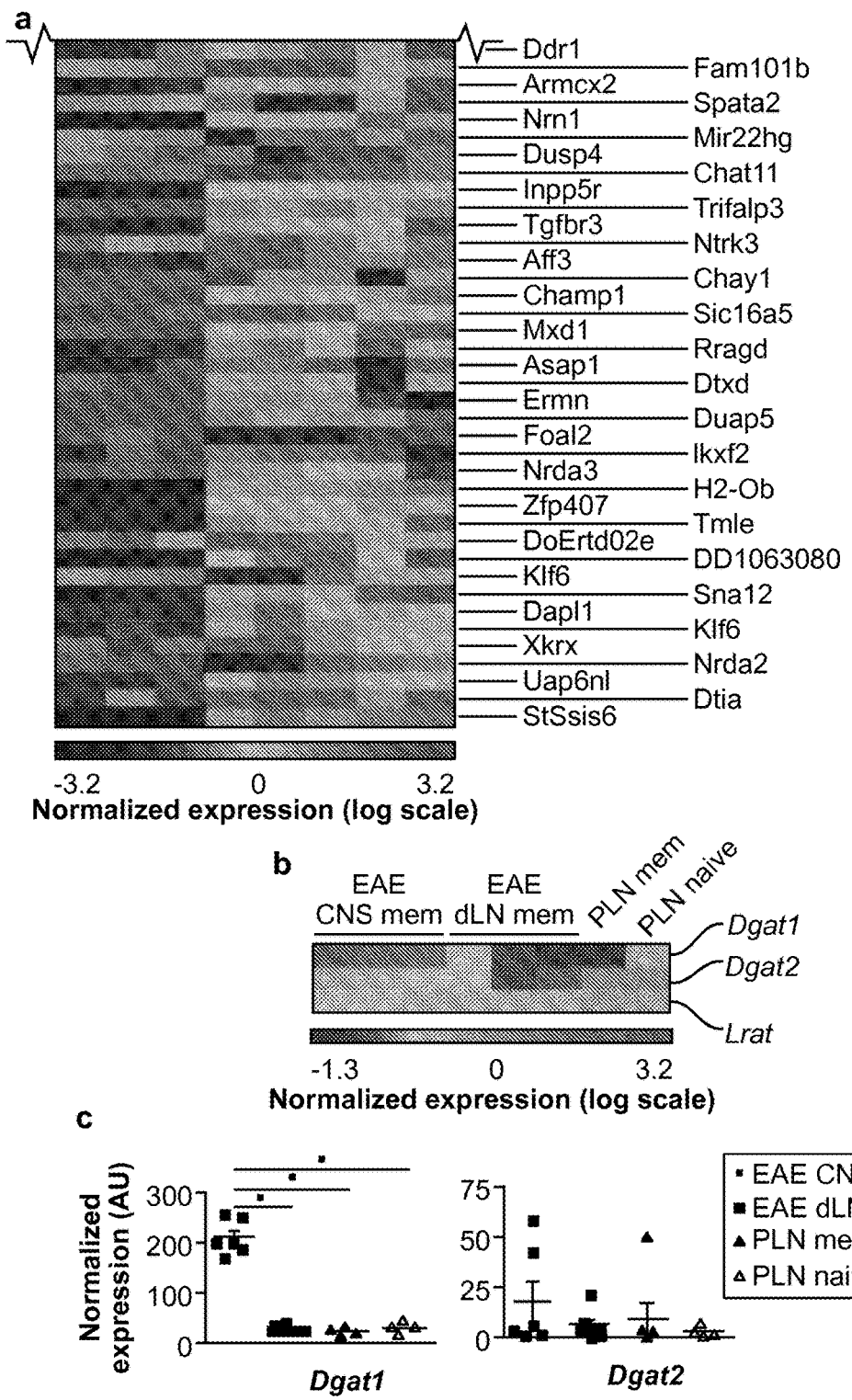

Transcripts for lecithin:retinol acyltransferase (Lrat), another enzyme with activity that overlaps with DGAT1, were not detectable in naive or memory phenotype T cells (FIG. 2b). Thus, DGAT1 may represent a "metabolic checkpoint" for activated T cells within the CNS.

Pharmacologic DGAT1 Inhibition Ameliorates EAE.

Figure 3:
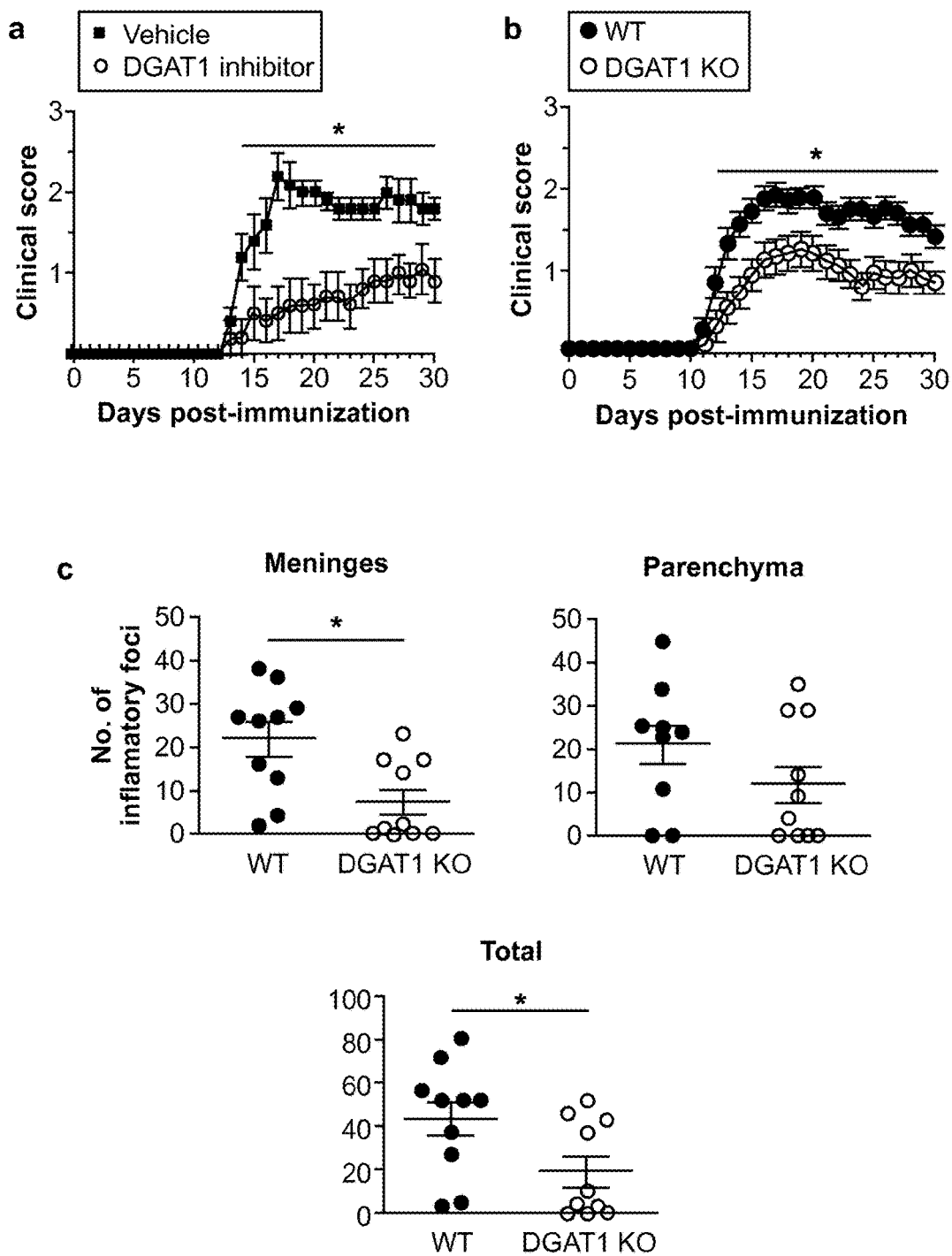
FIG. 3. DGAT1 pharmacologic inhibition and genetic deficiency modulate EAE. (a) C57BL/6 mice were induced to develop EAE by active immunization with $MOG_{35-55}$/CFA, and then followed daily for clinical signs. Beginning at day 12 p.i. (arrow), mice were administered vehicle or 10 mg/kg DGAT1 inhibitor via s.c. injection once daily. Clinical data are presented as mean score ±SEM. *$P<0.05$ (days 14-30 p.i.) by Mann-Whitney U test. (b) C57BL/6 WT and DGAT1 KO mice were induced to develop EAE by active immunization with $MOG_{35-55}$/CFA (n=25/group for days 0-17 pi; n=20/group for days 18-30 pi.). *$P<0.05$ for day 12-30 p.i., by Mann-Whitney U test. (c) Histological changes in meninges and parenchyma at day 30 p.i. were evaluated as described in the Methods section (Total=Meninges+Parenchyma). Bars represent mean±SEM. *$P<0.05$ by Student's t test.

The upregulation of Dgat1 by CNS-infiltrating CD4+ T cells in mice with EAE suggested that DGAT1 might play a role in regulating T cell functions during neuroimmune responses. To address this possibility, we first determined whether pharmacological inhibition of DGAT1 could modulate clinical EAE. Mice induced to develop EAE were administered vehicle or A922500, a selective DGAT1 inhibitor [MW=428 Da; $IC_{50}$: 24 nM for mouse DGAT1], beginning just prior to the onset of clinical signs (day 12 p.i.). A922500 did not induce overt behavioral changes or significantly alter leukocyte numbers or composition within peripheral lymphoid tissues. The drug also did not cause detectable organ toxicity, as determined by assessing wet weights and gross morphology of several organs, including lymphoid organs such as spleen and thymus. We found, however, that daily administration of 10 mg/kg A922500—which significantly reduces serum TG levels in models of obesity—attenuated EAE. Suppression of clinical disease was evident as early as 2 days after dosing began and persisted until termination of the experiment at day 30 p.i. (FIG. 3a). Overall, the compound delayed onset of clinical signs by an average of 6 days and reduced disease incidence at day 30 p.i. by 30%. Mice treated with DGAT1 inhibitor also had fewer CNS inflammatory cell infiltrates than their vehicle-treated counterparts, although these differences did not achieve statistical significance (Table 4). Thus, administration of a selective DGAT1 inhibitor attenuates EAE.

DGAT1 Deficiency Attenuates EAE.

Figure 9:
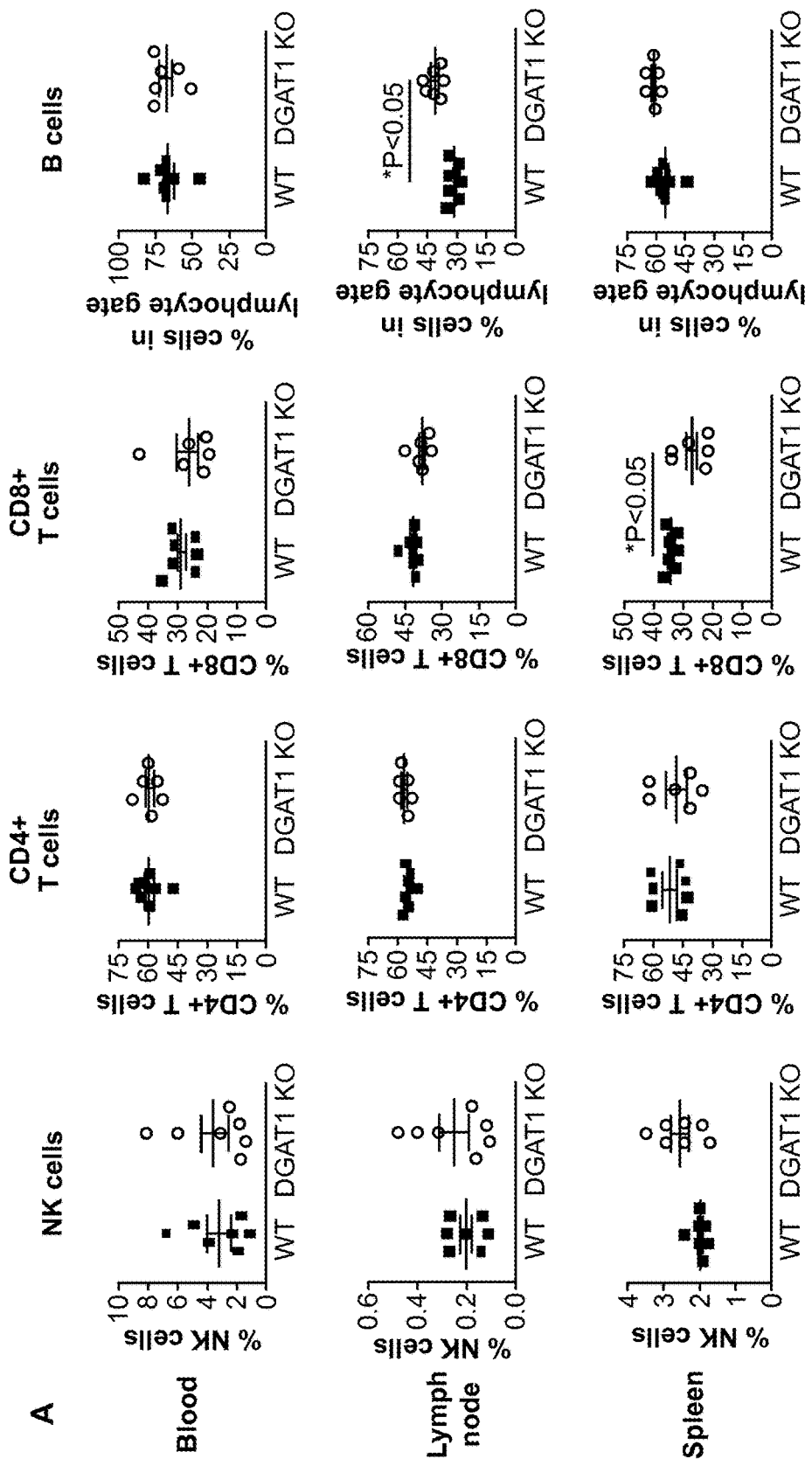
FIG. 9. Phenotypic analysis of lymphocyte distribution. Lymphoid tissues and peripheral blood leukocytes were harvested from naive male WT C57BL/6 mice or DGAT1 KO mice (10-12 weeks old). Cells were stained with fluorophore-labeled mAbs to identify the indicated lymphocyte subsets and data were acquired on a flow cytometer. Scatter plots indicate cell percentages (A) or total cell numbers (B). Each symbol represents an individual mouse, and bars depict the mean±SEM. *$P<0.05$ by Student's t test.
Figure 9:
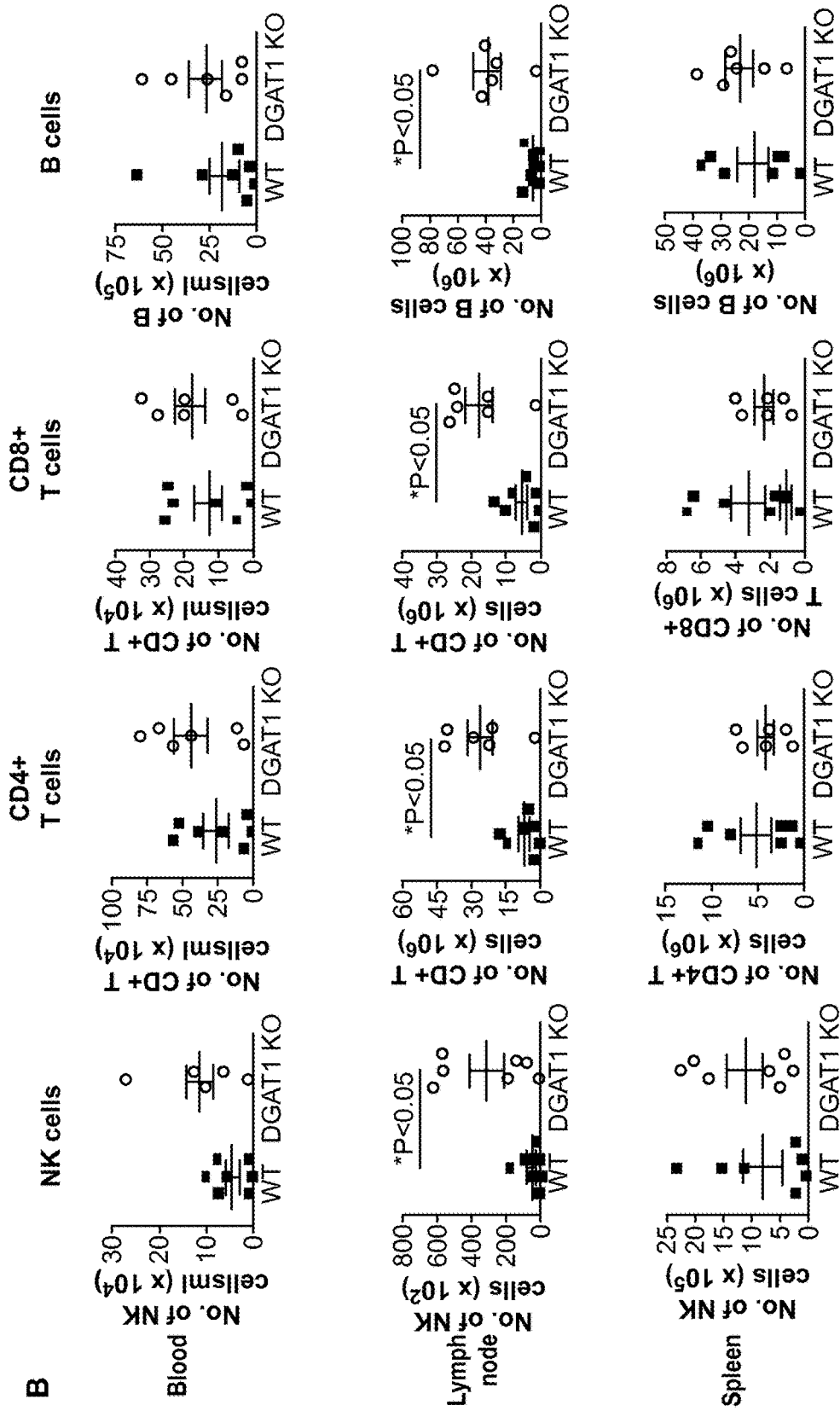
Figure 10:
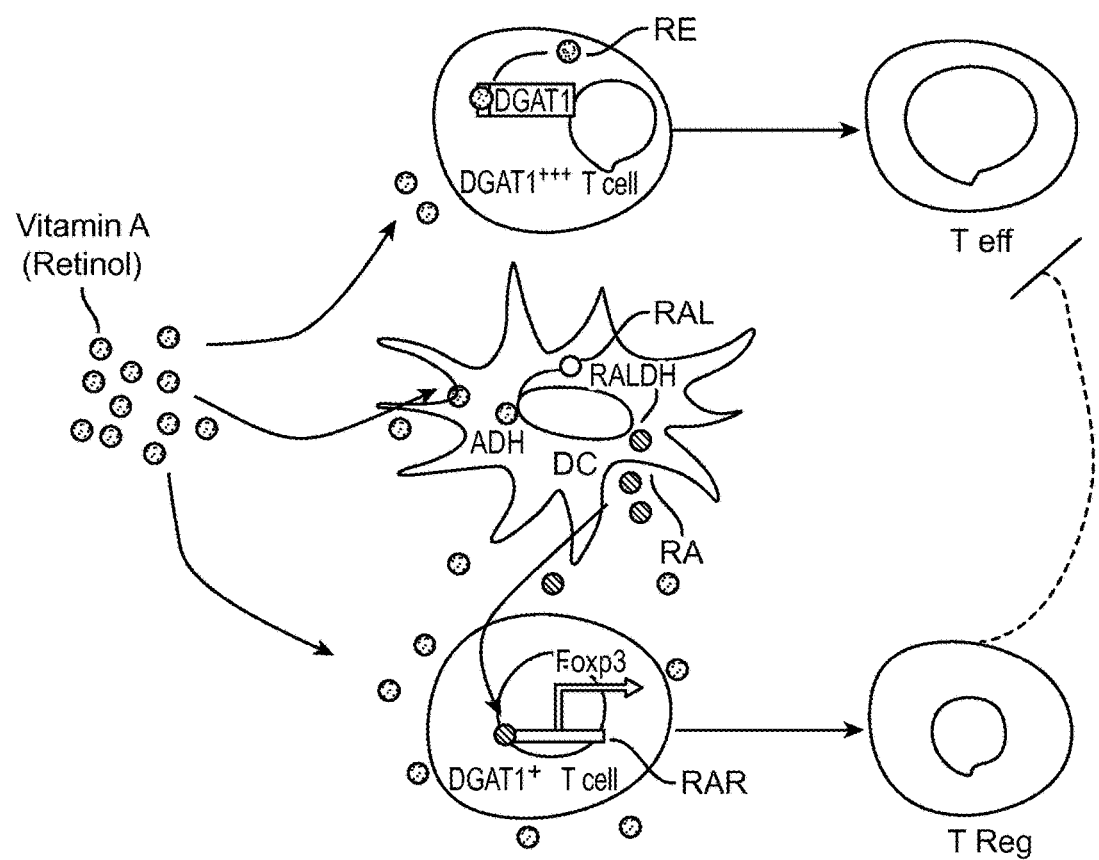
FIG. 10. Model for regulation of retinoic acid and Treg induction by T cell-expressed DGAT1. Vitamin A (retinol) enters through the diet. Dendritic cells (DC) and stromal cells express alcohol dehydrogenase (ADH) and retinal dehydrogenase (RALDH) enzymes that are required for oxidizing retinol to retinal (RAL), and from RAL to retinoic acid (RA), respectively. DGAT1-expressing T cells (DGAT1+/+) divert retinol to its retinyl ester (RE) form, which limits the availability of RA locally. In cases of DGAT1 inhibition or DGAT1 deficiency (DGAT1−/−), retinol is fully processed to RA. RA, through binding to the retinoic acid receptor (RAR), promotes induction of Foxp3+ Tregs, which suppress the activity of pathogenic T effector cells (T eff).

We also evaluated DGAT1 knockout (KO) mice for susceptibility to EAE. DGAT1 KO mice display resistance to diet-induced obesity and increased energy expenditure, but little is known about immune system function in these mice. We found that PLNs from naive DGAT1 KO mice contained more natural killer cells (NK1.1+TCRβ−), T cells (CD4+ and CD8+), and B cells than their WT counterparts, consistent with increased numbers (relative to WT) of total cells in this tissue (FIG. 9). However, anti-CD3/anti-CD28 stimulated DGAT1 KO and WT CD4+ T cells proliferated and produced IL-2 and IFNγ at similar levels, suggesting that DGAT1 deficiency does not cause overt defects in immune system development or T cell functions.

We found that DGAT1 KO mice developed less severe clinical EAE than their WT counterparts (FIG. 3b). To define potential roles for DGAT1 in leukocyte accumulation within and/or migration to the CNS, we evaluated neural tissues from mice with symptomatic EAE for inflammatory cell infiltrates. Consistent with the clinical findings, CNS tissues isolated from DGAT1 KO mice at day 30 p.i. contained fewer inflammatory foci than their WT counterparts (FIG. 3c).

Role of DGAT1 in EAE Induced by Adoptive Transfer.

Figure 4:
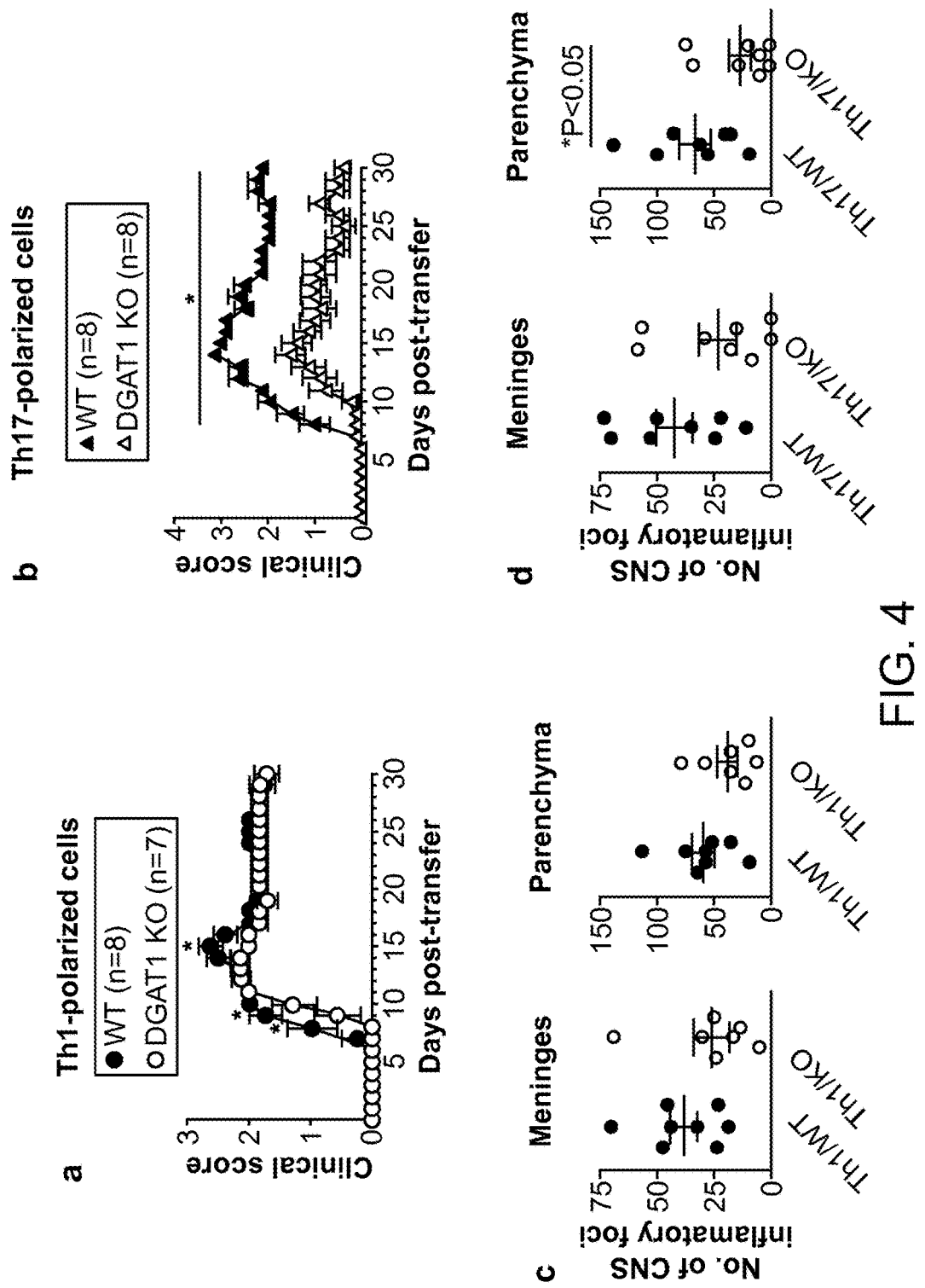
FIG. 4. DGAT1 promotes induction of Th17-EAE by adoptive transfer. Naive C57BL/6 WT mice were injected with $MOG_{35-55}$-reactive WT or DGAT1 KO CD4+ T cells differentiated in vitro under (a) Th1 (b) or Th17 polarization conditions. Mice were followed for clinical signs. Data are pooled from two independent experiments (n=3-5 recipient mice/group for each experiment), and are presented as mean clinical score ±SEM. *$P<0.05$ by Mann-Whitney U test. Histological changes in CNS tissues isolated at 30 days post-transfer from mice that received (c) Th1- or (d) Th17-polarized cells were evaluated as described in Methods.

To determine the role of DGAT1 in the induction of EAE by encephalitogenic CD4+ T cells, we utilized passive transfer models of disease. We injected naive WT mice with MOG-reactive DGAT1 KO or WT CD4+ T cells, which were differentiated in vitro under Th1- or Th17-polarization conditions. DGAT1-deficient Th1 cells induced EAE capably in WT recipients, but the onset of clinical signs was delayed by 1.5 days (FIG. 4a). There were, however, no significant differences in the CNS histological changes induced by WT vs. DGAT1 KO Th1 cells at 30 days post-transfer (FIG. 4c). DGAT1 deficiency in Th17 cells had a more pronounced effect on the induction of disease by passive transfer. In mice that received DGAT1 KO Th17 cells, EAE onset was delayed by 2.5 days, and the severity of clinical disease was significantly reduced (from day 8 post-transfer onwards) compared to mice that were injected with WT Th17 cells (FIG. 4b). Mice that received DGAT1 KO Th17 cells also had significantly fewer inflammatory foci within the CNS parenchyma than mice that received WT Th17 cells at 30 days post-transfer, suggesting that DGAT1 regulates Th17 cell trafficking to and/or activation within the CNS (FIG. 4d). These results show that DGAT1 acts at least in part cell intrinsically in T cells to regulate encephalitogenic potential of in vitro-polarized Th17 cells.

DGAT1 is not Required for IFNγ+ or IL-17+ CD4+ T Cell Induction.

To define potential mechanisms for the reduced EAE in DGAT1 KO mice, we evaluated leukocyte distribution and localization, as well as lymphocyte effector responses. WT and DGAT1 KO CNS tissues from mice with EAE contained statistically indistinguishable numbers of CD4+ T cells at day 17 p.i.; however, upon ex vivo restimulation with $MOG_{35-55}$ peptide, CNS mononuclear cells (MNCs) from WT mice with EAE produced pro-inflammatory cytokines (e.g., IFNγ, IL-17, IL-6, TNF) at levels that trended higher than their DGAT1 KO counterparts. These differences, however, did not achieve statistical significance for any of the $MOG_{35-55}$ concentrations tested. Similarly, DGAT1 KO and WT dLN CD4+ T cells produced comparable levels of IFNγ and IL-17.

Figure 5:
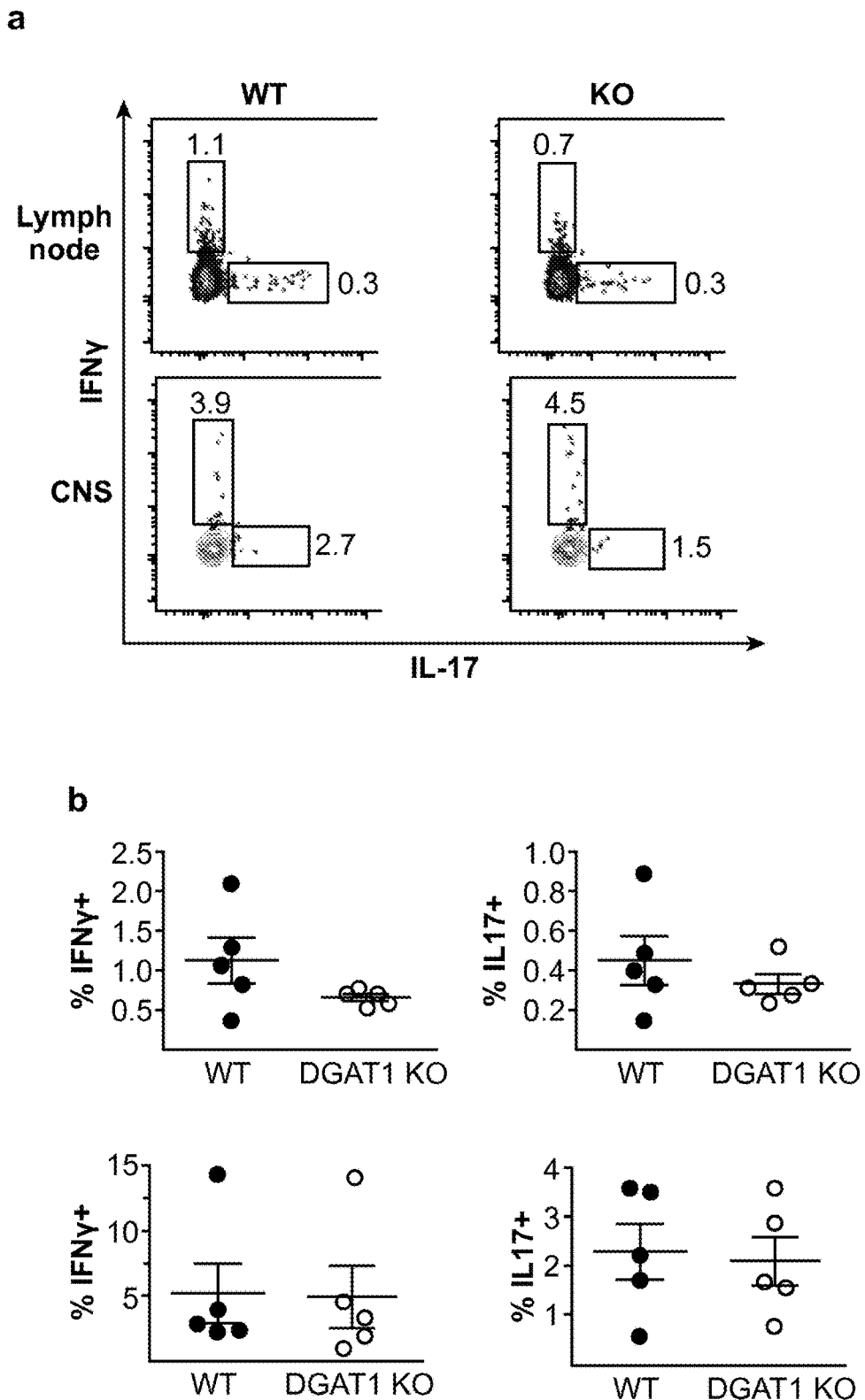
FIG. 5. DGAT1 does not impact induction of IFNγ- or IL17-producing CD4+ T cells. Male WT and DGAT1 KO mice (n=5/group) were induced to develop EAE. At day 17 p.i., mice were killed; dLN cells (top panels) or CNS MNCs (bottom panels) were then stimulated for 72 hr with 20 μg/ml of $MOG_{35-55}$. PMA/ionomycin and protein transport inhibitor were added for the last 5 hours of the culture period. Cells were then stained with mAbs to surface markers and intracellular cytokines and analyzed by flow cytometry. Viable lymphocytes were gated as NK1.1-CD4+ and evaluated for IFNγ and IL-17 expression. (a) Representative FACS plots indicate the percentage of CD4+ T cells that stained positive for IFNγ or IL-17 in WT and DGAT1 KO dLNs and CNS. (b) Scatter plots indicate the percentage of IFNγ+ (left) and IL-17+ (right) CD4+ T cells in WT and DGAT1 KO tissues. Each symbol represents an individual mouse; the bar depicts the mean±SEM. None of the differences achieved statistical significance.

We also evaluated MOG-recall cytokine-producing T cell frequency in CNS and LN tissues from WT and DGAT1 KO mice with EAE. Consistent with the cytokine secretion data, there was no significant difference between WT and DGAT1 KO CNS tissues with respect to absolute numbers or relative frequency of IL-17+ or IFNγ+ CD4+ T cells; and DGAT1 KO and WT draining LNs contained similar numbers and percentages of IFNγ-producing and IL-17-producing CD4+ T cells (FIG. 5a, FIG. 5b). Thus, DGAT1 does not appear to significantly influence Th1 or Th17 cell induction in vivo during EAE.

Treg Distribution in DGAT1 KO Tissues.

Figure 6:
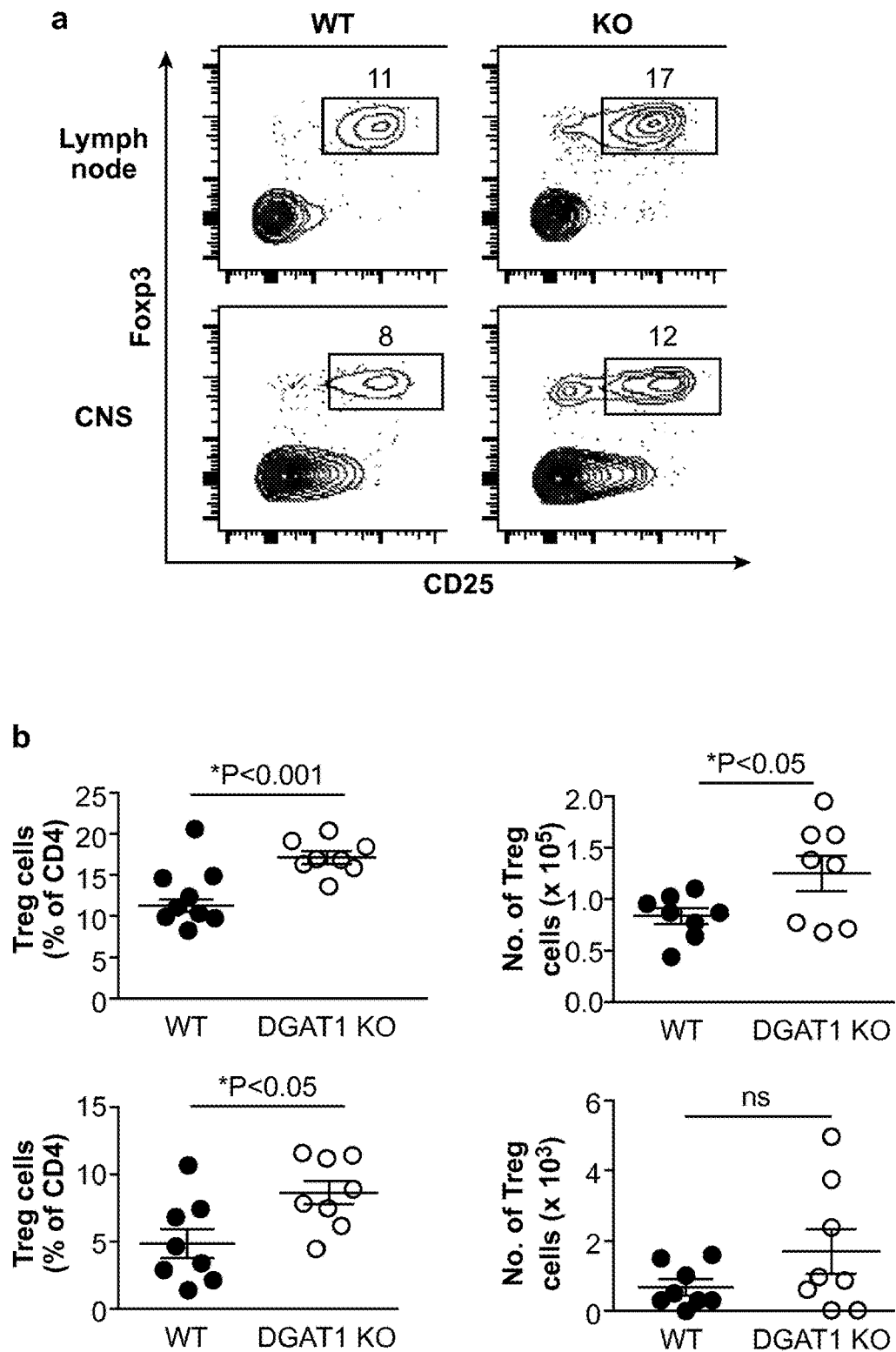
FIG. 6. DGAT1 KO tissues contain a higher frequency of Treg cells. Male C57BL/6 and DGAT1 KO mice (n=8/group) were induced to develop EAE by immunization with $MOG_{35-55}$/CFA. At day 17 p.i., mice were killed and cells in dLN or CNS tissues were analyzed by flow cytometry. NK1.1-CD4+ lymphocytes were then analyzed for expression of CD25 and Foxp3. (a) Representative FACS plots indicate the frequency of CD25+Foxp3+ Tregs in dLN and CNS tissues of WT and DGAT1 KO mice. Numbers represent the percentage of Tregs within the gate. (b) Scatter plots indicate the percentage (left) or number (right) of CD4+ Tregs in WT and DGAT1 KO tissues. Each symbol represents an individual mouse; the bar depicts the mean±SEM. *$P<0.05$ by Student's t test. ns, not significant.

Tregs are key determinants of immunopathology in EAE. We therefore evaluated WT and DGAT1 KO CD4+ T cells in tissues from mice with EAE for expression of the Treg lineage marker Foxp3. We found that dLNs and spleens, as well as CNS tissues from DGAT1 KO mice with EAE contained a significantly higher percentage of CD25+ Foxp3+ Tregs than their WT counterparts (FIG. 6a, FIG. 6b). In addition, spleens and PLNs from naive DGAT1 KO mice contained a higher proportion of Tregs than WT controls, suggesting that DGAT1 may limit Treg development and/or expansion during both homeostasis and immunity. Collectively, the higher relative proportion of Tregs in DGAT1 KO tissues is consistent with the attenuated clinical EAE exhibited by DGAT1 KO mice.

T Cell-Expressed DGAT1 Limits Retinol-Dependent Treg Induction In Vitro.

DGAT1 possesses acyltransferase activity towards a number of substrates, including retinol. This acyl-CoA:retinol acyltransferase (ARAT) function enables DGAT1 to convert retinol (vitamin A) to its storage retinyl ester form. RA, the active metabolite of vitamin A, supports Treg induction; however, T lymphocytes cannot synthesize RA autonomously. We hypothesized that T cell-expressed DGAT1 functions as an ARAT, diverting retinol to its storage ester form. This would lead to a reduction in levels of RA locally. Conversely, DGAT1 deficiency would prevent this sequestration of retinol, leading to elevated RA and Treg induction. To test this possibility, we stimulated WT or DGAT1 KO CD4+CD25− T cells (i.e., "non-Tregs") with anti-CD3/ TGFβ in the presence of mesenteric lymph node (MLN) antigen presenting cells (dissociated MLN cells depleted of T cells). Dendritic cells (DCs) and stromal fibroblastic reticular cells (FRC) in MLN express high levels of the alcohol dehydrogenase and retinal dehydrogenase enzymes necessary for converting retinol to RA; however, MLN stromal FRC also express potentially significant levels of Dgat1 message (Immunological Genome Project Data). Thus, we used MLN cells from DGAT1 KO mice as antigen presenting cells, to ensure that any potential DGAT1-mediated retinyl ester generation was derived from the T cell compartment. We also cultured cells in retinoid-free ("delipidated") serum.

Figure 12:
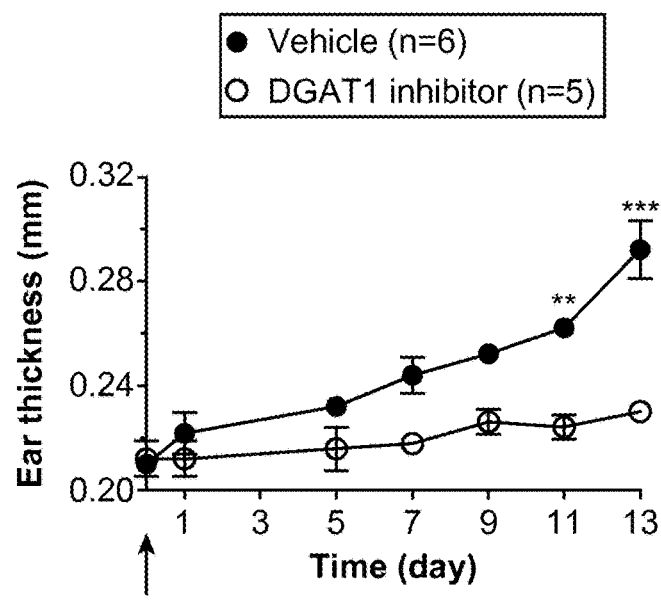
FIG. 12. Pharmacologic DGAT1 inhibition suppresses IL-23-induced ear swelling.

We found that in vitro anti-CD3/TGFβ treatment induced Tregs with similar efficiency from WT and DGAT1 KO naive (CD25-) T cell precursors. Addition of physiological levels of retinol (10 nM) to the culture significantly enhanced Foxp3+ Treg induction from DGAT1 KO (DGAT1−/−), but not from WT (DGAT1+/+) CD4+CD25− T cells, consistent with an inhibitory role for DGAT1 in retinoic acid signaling. Addition of the DGAT1 inhibitor A922500 abrogated the difference between DGAT1−/− and WT cell responses. Moreover, DGAT1 deficiency had no significant effect on enhanced Treg induction by the synthetic RAR agonist AM580 (FIG. 7a, FIG. 7B) T cells derived from males and females yielded similar results in this assay. The results suggest that T cell-expressed DGAT1 acts in a cell-intrinsic manner to limit Treg formation when retinol is present, presumably by retinol esterification and sequestration (FIG. 12).

Large-scale transcriptional profiling can define novel mechanisms that contribute to the development and evolution of complex disease processes. For example, microarray analysis of histologically characterized MS plaques identified several genes that were uniquely transcribed in acute active versus chronic silent lesions. The therapeutic relevance of select candidate genes was subsequently validated in EAE. More recently, comparative proteomics and transcriptomic studies have uncovered additional regulatory pathways and pathogenic mechanisms in EAE and MS. The clinical and histological heterogeneity of MS, however, presents challenges for applying "omics" approaches to identify tractable therapeutic targets. Here, we focused our analyses on discrete T lymphocyte subsets within the CNS and lymphoid tissues of mice with EAE. We report that memory phenotype CD4+ T cells isolated from spinal cords of mice with acute clinical EAE express high levels of mRNA for Dgat1. Parenteral administration of a pharmacologic DGAT1 inhibitor, as well as genetic DGAT1 deficiency, attenuated EAE; and healthy mice that received encephalitogenic, in vitro-polarized DGAT1 KO Th17 cells exhibited delayed EAE onset and reduced disease (compared with mice that received WT Th17 cells), indicating a cell-intrinsic role for T cell-expressed DGAT1 in EAE pathology. In addition, CNS and lymphoid tissues from DGAT1 KO mice contained a higher proportion of Treg cells, consistent with our observations of more efficient in vitro Treg induction from naive DGAT1 KO CD4+ T cells in the presence of physiological concentrations of retinol. DGAT1 is closely related to a second diacylglycerol acyltransferase, DGAT2. Both enzymes catalyze the final and essential step in triglyceride (TG) synthesis, but only DGAT2 is essential in vivo. We did not, however, detect significant Dgat2 message in T cells. Moreover, DGAT2 lacks ARAT or other acyltransferase activity.

Figure 7:
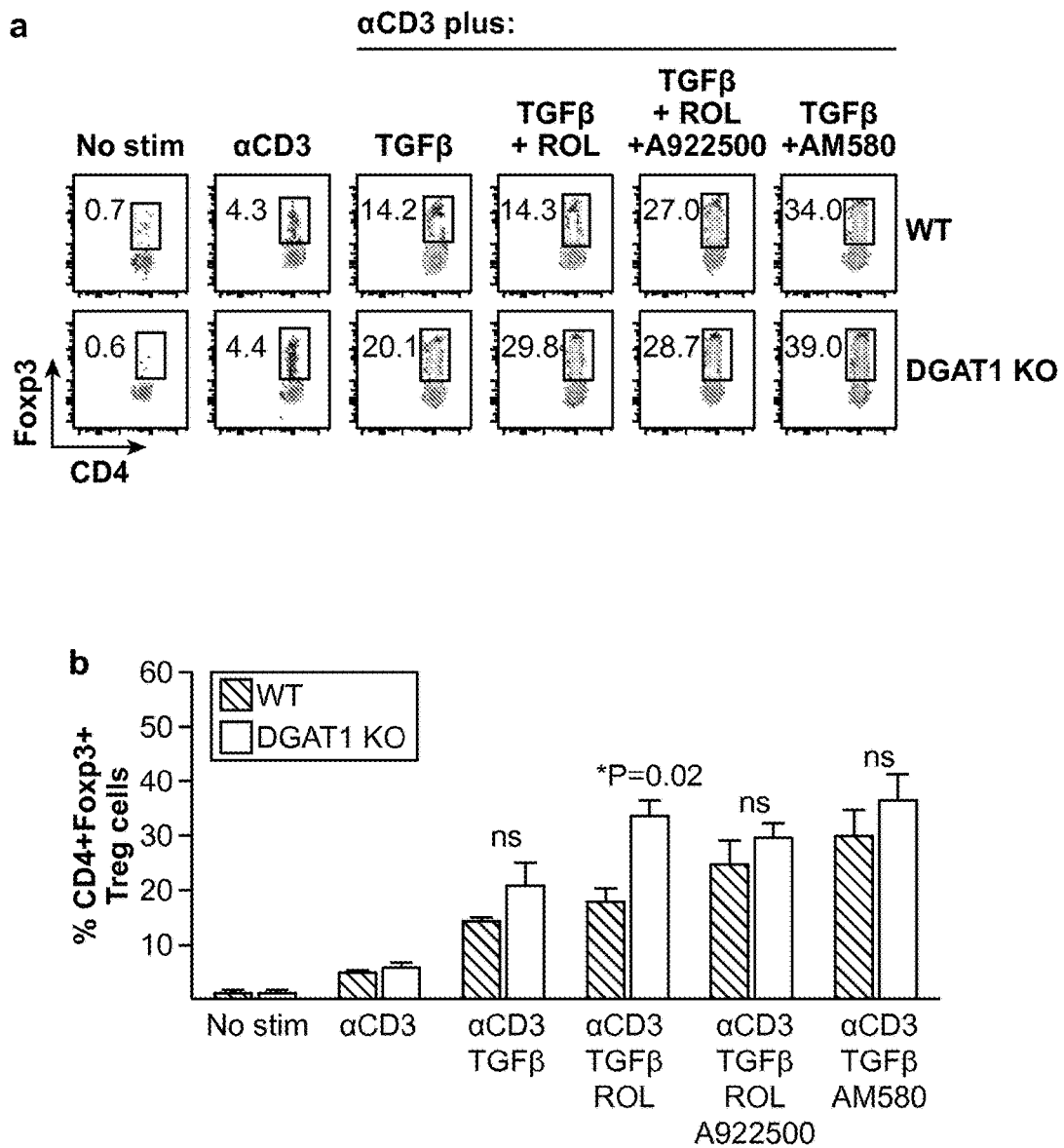
FIG. 7. DGAT1 limits retinoic acid-dependent Treg induction. WT or DGAT1 KO CD4+CD25− cells were incubated with T cell-depleted DGAT1 KO MLN cells in delipidated serum in the absence or presence of: soluble anti-CD3; TGFβ; retinol (ROL; 10 nM); A922500 (100 nM); or AM580 (10 nM) where indicated. After 3 days, TCRβ+ lymphocytes in the live gate were analyzed for expression of CD4 and Foxp3 by flow cytometry. (a) Representative FACS plots show the frequency of WT (top panels) or DGAT1 KO (bottom panels) CD4+Foxp3+ Tregs within the gate. (b) FACS data are summarized in bar graph form. Bars depict the mean+SEM of triplicate wells. Two independent experiments were performed.
Figure 8:
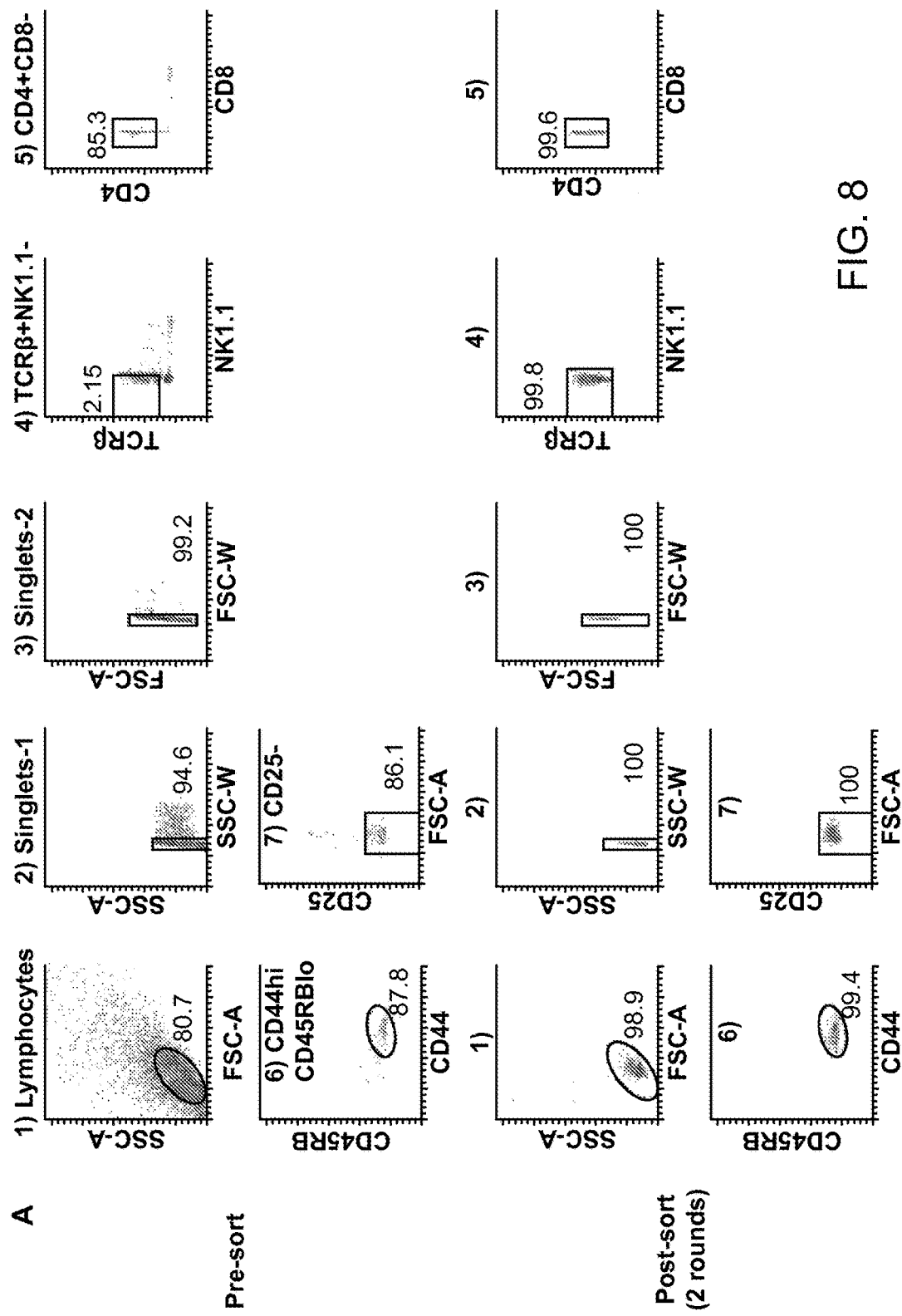
FIG. 8. Analysis of FACS-sorted CD4+ T cell purity. Memory phenotype CD4+ T cells (NK1.1-TCRβ+CD4+CD8-CD44hiCD45RBloCD25−) were sorted from (A) CNS and (B) dLN tissues of mice with EAE as described in the Methods section. FACS plots depict the sorting scheme and cell purity prior to sorting (Pre-sort) and again after 2 rounds of sorting (Post-sort). Similar purity was achieved for memory and naive (CD44loCD45RBhiCD25−) phenotype CD4+ T cells sorted from PLNs of naive C57BL/6 mice.
Figure 8:
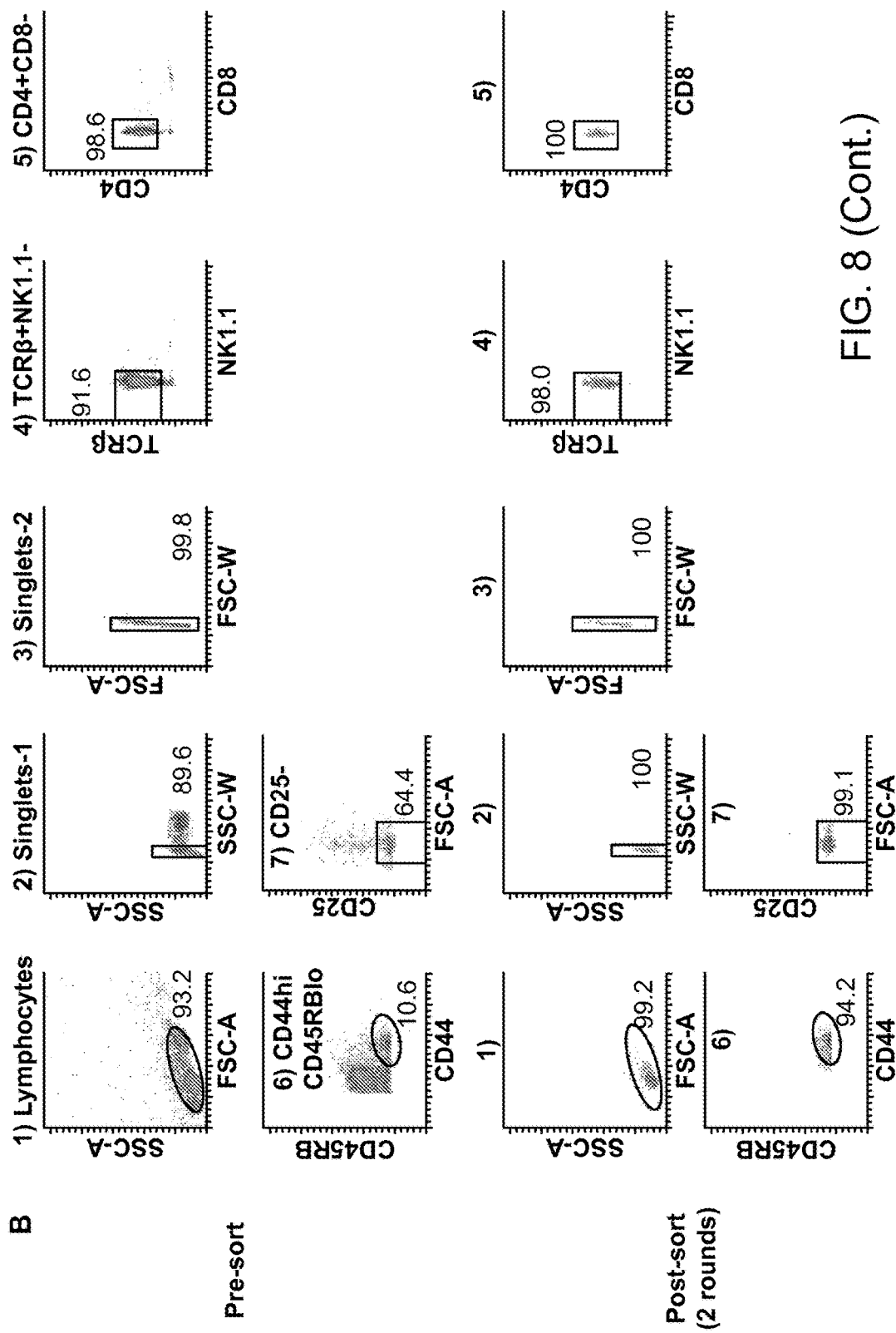

Vitamin A, a dietary, fat-soluble vitamin, is converted to retinal and then to retinoic acid (RA). The binding of RA to specific retinoic acid receptors (RARs) has myriad effects on gene transcription and cellular differentiation. Levels of retinol and RA are therefore tightly regulated. For example, in the epidermis, the ARAT function of DGAT1 prevents accumulation of RA and consequent development of alopecia when excess retinol is present. Lecithin:retinol acyltransferase (LRAT), which like DGAT1 converts retinol to retinyl esters, is the enzyme responsible in most tissues for retinol storage under homeostatic conditions. Naive and activated T cells, however, do not express detectable Lrat message (FIG. 2b and Immunological Genome Project data). We hypothesized that DGAT1 deficiency or inhibition results in accumulation of RA, thereby promoting induction of Tregs that can limit pathology in EAE/MS. Consistent with this possibility, we observed enhanced Treg induction by DGAT1 KO CD4+CD25− T cells when incubated with TGFβ in the presence of physiological concentrations of retinol in vitro (FIG. 7a, FIG. 7b). We attribute this finding to the ability of T cell-expressed DGAT1—via its putative ARAT function—to limit RA levels locally (FIG. 12), but other DGAT1-dependent mechanisms are not excluded. Therapeutic administration of RA suppresses clinical EAE; however, in this context, the primary effect of RA may be to inhibit Th17 differentiation, rather than to enhance Treg frequency. Incidentally, low serum levels of retinol are associated with increased MS risk, and serum retinol levels are inversely correlated with MRI activity in MS.

To meet the energetic demands of clonal expansion, activated T cells reprogram their metabolism, resulting in a shift from β-oxidation of fatty acids in naive T cells, to increased utilization of glycolytic, pentose-phosphate, and glutaminolytic pathways. Lipid metabolism pathways can also function as regulators of activated lymphocyte function and differentiation. Our results support a role for T cell-expressed DGAT1 in limitation of retinoid-induced T cell functions including Treg induction. DGAT1 has diverse enzymatic activities that have the potential to regulate T cell activity and functional outcomes on multiple levels. For example, DGAT1 catalyzes formation of triglycerides (TGs), a major form of neutral lipid that serves as an important energy storage molecule in mammalian cells. We found that extracts from activated CD4+ T cells synthesized detectable levels of TGs from diacylglycerol and oleoyl-CoA in vitro, demonstrating the presence of functional DGAT enzyme in these cells (not shown). Similarly, it has recently been shown that CD8+ memory T cells contain TGs, which are presumed to undergo lipolysis. Fatty acids stored as TGs can also be utilized for membrane lipid synthesis, and DGAT1-mediated esterification of fatty acids into neutral lipids can protect cells from fatty acid cytotoxicity. In this context, DGAT1 could protect pathogenic effector T cells within the CNS from lipotoxicity, providing another potential mechanism for the attenuated EAE phenotype in DGAT1 KO mice.

The recent demonstration that Treg and Th17 cells exhibit differential dependence on de novo fatty acid synthesis highlights fundamental roles for lipid metabolism pathways in T cell development and differentiation. Our results indicate that encephalitogenic Th17 cells require DGAT1 for maximal induction of EAE upon adoptive transfer into immunocompetent hosts. It is not clear, however, whether this is due to DGAT1 effects on Th17 cell trafficking to the CNS, cellular activation within the CNS, or a combination of these effects. Further investigation of potential roles for DGAT1 in regulating Th17 cell functions is warranted. This question is also clinically relevant, as the relative activity of Th1 and Th17 cells—which have distinct roles in EAE development and progression—is a predictor of MS patient responses to β-interferon, a widely used frontline MS therapeutic. Understanding metabolic factors that control Th17 cell induction and effector functions is therefore likely to inform the development of effective targeted therapies for MS and other Th17-mediated diseases.

The ability of a pharmacologic DGAT1 inhibitor to attenuate clinical EAE provides a proof-of-concept demonstration that this enzyme may be a viable target for therapy of autoimmune demyelinating disease. Although we began dosing with the inhibitor before the appearance of overt clinical signs (mean day of disease onset in vehicle-treated mice=14.2, while dosing began at day 12), CNS cellular activation and T lymphocyte infiltration of the CNS precede development of clinical EAE. Thus, the ability of the inhibitor to attenuate EAE when administered therapeutically may be due to contemporaneous effects on cells within the CNS (both resident and recruited) and metabolic influences on inflammatory cell activation within the periphery.

In this study, we focused on roles for DGAT1 in T cell-mediated pathology and effector functions, but we do not exclude roles for DGAT1 in other immune cells. For example, neutrophils, which express significant levels of Dgat1 message (Immunological Genome Project data), can also contribute to pathology during EAE. However, we observed no difference in the ability of WT encephalitogenic T cells to induce EAE in WT versus DGAT1 KO hosts. This further underscores critical roles for T cell-expressed DGAT1 in EAE pathology.

In summary, we demonstrate that memory CD4+ T lymphocytes upregulate Dgat1 message during autoimmune CNS inflammation, and that DGAT1 pharmacologic inhibition and genetic deficiency significantly ameliorate EAE. In addition, T cell-expressed DGAT1 limits retinol-mediated Treg formation in vitro. These results add to the growing appreciation of the interplay between immune and metabolic pathways. They also suggest that DGAT1 inhibitors, currently in trials for metabolic diseases, should be assessed for roles in therapy of MS and potentially other disorders associated with Th17 or Treg cell imbalance.

Methods

Mice and reagents. All animal experiments were conducted in accordance with approved NIH and IACUC guidelines. C57BL/6 WT and DGAT1 KO mice were purchased from The Jackson Laboratory. Myelin oligodendrocyte glycoprotein (MOG) peptide amino acids 35-35 (MEVGWYRSPFSRVVHLYRNGK; $MOG_{35-55}$) was synthesized by the Stanford Protein and Nucleic Acid Facility (Stanford, Calif.). The DGAT1 inhibitor A922500 was purchased from Selleck Chemical Company. Captisol (Cydex Pharmaceuticals), a modified cyclodextrin that has a favorable drug formulation profile, was used as the vehicle for A922500. Normal FBS was from HyClone, and delipidated FBS was from Gemini Bio-Products. Cell culture media ("complete RPMI") consisted of RPMI 1640 supplemented with 10% FBS (normal or delipidated), penicillin/streptomycin, L-glutamine, minimum non-essential amino acids, sodium pyruvate, 20 mM HEPES buffer, and 50 µM 2-mercaptoethanol. Antibodies directed against TCRβ (H57-597), NK1.1 (PK136), CD25 (PC61), CD44 (IM7), CD45RB (C363.16A), Foxp3 (FJK-16s), CD4 (RM4-5), CD8 (53.6-7), CD3ε (145-2C11), IFNγ (XMG1.2) and IL-17A (TC11-18H10) were from eBioscience or BD Biosciences; and fixable cell viability dye was from eBioscience. FlowJo software (TreeStar) was used for analysis of flow cytometry data. Phorbol 12-myristate 13-acetate (PMA) and ionomycin (Sigma) were used at 50 ng/ml and 500 ng/ml, respectively. Protein transport inhibitor (containing monensin and brefeldin A) was from eBioscience. Recombinant mouse IL-12, IL-23 and TGFβ were from R&D Systems. All-trans-retinol was from Sigma, and AM580 was from Tocris Biosciences. Where indicated, T cell-depleted MLN cells ($5\times10^6$ cells/ml) were incubated with 50 µg/ml mitomycin C (Sigma) for 20 min at 37° C. Cells were then extensively washed in PBS, followed by co-incubation with WT or DGAT1 KO CD25− T cells in U96 plates (37° C., 5% $CO_2$).

EAE models. For EAE induction by active immunization, mice (8-10 weeks old) were immunized via subcutaneous (s.c.) injection with 100 µg $MOG_{35-55}$ emulsified in CFA as described. Mice also received 250 ng pertussis toxin (List Biological Labs) via tail vein injection at the time of $MOG_{35-55}$/CFA immunization and again 2 days later. Clinical disease was scored as follows: 0=normal or healthy; 1=flaccid tail; 2=hindlimb weakness; 3=hindlimb paralysis; 4=hindlimb and forelimb paralysis; 5=moribund or dead. Where indicated, A922500 was formulated in 10% Captisol vehicle for in vivo dosing via s.c. injection (100 µl volume). Individuals who conducted the clinical scoring were blinded to the treatment that the mice received.

For EAE induction by adoptive transfer, WT or DGAT1 KO mice were immunized s.c. with $MOG_{35-55}$/CFA. Mice received 250 ng pertussis toxin via intraperitoneal injection at the time of $MOG_{35-55}$/CFA immunization and again 2 days later. Ten days after immunization, spleens and dLN cells (i.e., inguinal LN) were harvested, pooled and resuspended in complete RPMI at $5\times10^6$ cells/ml. Cells were incubated with $MOG_{35-55}$ (10 µg/ml) plus: i) IL-23 (10 ng/ml) to generate Th17-polarized cells; or ii) IL-12 (10 ng/ml) to generate Th1-polarized cells. After 72 hr in culture (37° C., 5% $CO_2$), cells were washed extensively with PBS, and then resuspended in PBS before i.p. injection into healthy, naive C57BL/6 mice (8-10 weeks old, $5\times10^6$ cells/mouse).

Cell sorting and microarray analysis. For transcriptional profiling of T cells from mice with MOG-induced active EAE, dLN and spinal cord tissues were harvested and pooled (n=20-25 mice per experiment, 3 independent experiments) at the time of peak acute disease [approximately 13-17 days post-immunization (p.i.)]. CNS mononuclear cells (MNCs) from spinal cords were isolated over 30%:70% discontinuous Percoll gradients. CD4+ T cells from dLN tissues of mice with EAE, as well as from pooled peripheral LNs (PLNs—axillary, brachial and inguinal) of naive C57BL/6 mice (8-10 weeks old), were isolated by negative selection with magnetic beads (Miltenyi). Memory CD4+ T cells (memCD4T; $CD44^{hi}CD45RB^{lo}CD25^-$) and naive phenotype ($CD44^{lo}CD45RB^{hi}CD25$) CD4+ T cells from LNs, as well as memCD4T derived from CNS MNCs were sorted on an Aria II instrument. RNA from FACS-sorted cells was isolated with a Qiagen RNeasy Kit, and 100-200 ng total RNA from each sample was used for amplification, labeling and hybridization on Affymetrix mouse 430 2.0 arrays by the Stanford Protein and Nucleic Acid Facility. Microarray data were analyzed using Gene- Spring GX 13.0 software. Gene expression values were normalized with the RMA16 algorithm of GeneSpring for the visualization and analysis of microarrays. Probes were then filtered by expression value (at least three out of the four conditions within the dataset—i.e., CNS memCD4T; EAE dLN memCD4T, PLN memCD4T; PLN naive—had to show an average raw value above 120). To enrich for highly differentially expressed genes within CNS-infiltrating T cells, genes in the CNS memCD4T cell subset with expression values that differed by at least fourfold (p<0.05, Benjamini-Hochberg correction) from the EAE dLN memCD4T cell subset were selected for additional analysis.

Real-time reverse transcriptase quantitative PCR (RT-QPCR). Total RNA from memory and naive phenotype CD4+ T cells was isolated by Trizol extraction, and gene expression was measured by RT-QPCR using a QuantiFast One-Step RT-PCR Kit (Qiagen) according to the manufacturer's instructions. Samples were analyzed using an Applied Biosystems 7900HT real-time PCR instrument. Mouse primer sequences were as follows: β-actin forward, 5'-GTATCCATGAAATAAGTGGTTACAGG-3'; β-actin reverse, 5'-GCAGTACATAATTTACACAGAAGCAAT-3'. DGAT1 forward, 5'-CCCATACCCGGGACAAAGAC-3'; DGAT1 reverse, 5'-ATCAGCATCACCACACACCA-3'. Primers for DGAT2 were used as described.

In vitro T regulatory cell induction. PLN tissues from C57BL/6 WT or DGAT1 KO mice (8-10 weeks) were depleted of CD4+CD25+ T cells by using a T regulatory cell isolation kit (Miltenyi). MLN tissues from sex-matched DGAT1 KO mice were depleted of T cells via CD90.2 magnetic beads (Miltenyi). CD4+CD25− cells ($10^5$) were then incubated with T cell-depleted, mitomycin C-treated MLN cells ($4 \times 10^4$) in the absence or presence of TGFβ (5 ng/ml), soluble anti-CD3 (0.25 μg/ml), A922500 or AM580. MLN cells were >99% free of T cells following CD90.2 bead depletion, and PLN cells were >99% CD4+CD25− following CD25+ cell depletion, as determined by flow cytometry.

Histology. Brain and spinal cord tissues were fixed in 10% buffered formalin. Paraffin-embedded tissues were then stained with H&E, and CNS inflammatory foci (>10 mononuclear cells/focus) in leptomeninges and parenchyma were counted in each mouse sample in a blinded fashion.

Statistics. The Mann-Whitney U test was applied to analyze nonparametric clinical EAE data, and the Student's t test was used to analyze all parametric data. The Fisher's exact test was used to compare disease incidence.

Example 3

Treatment of Psoriasis

Figure 11:
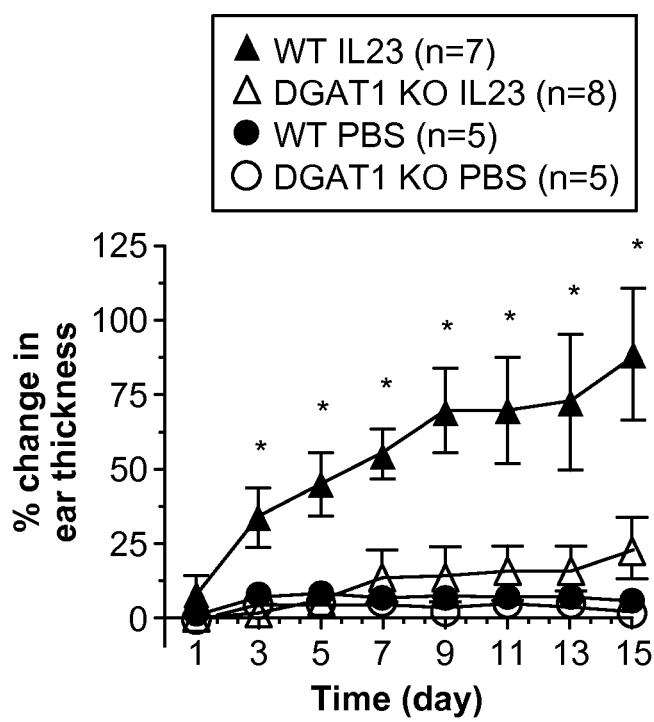
FIG. 11. Pharmacologic DGAT1 inhibition attenuates established IL-23-induced ear swelling.

Shown in FIG. 11, ears of male mice (8-15 weeks of age) were injected intradermally every other day with PBS or 500 ng recombinant IL-23. Beginning on day 5 (arrow), mice received 10 mg/kg of DGAT1 inhibitor A922500 (or 10% Captisol vehicle control) via subcutaneous injection. Mice continued to received drug or vehicle once daily for the duration of the experiment. Data are presented as mean ear thickness ±SEM. ***P<0.001 by ANOVA.

Ears of male mice (8-15 weeks of age) were injected intradermally every other day with PBS or 500 ng recombinant IL-23. Beginning on day 0 (arrow), mice received 10 mg/kg of DGAT1 inhibitor A922500 (or 10% Captisol vehicle control) via subcutaneous injection. Mice continued to received drug or vehicle once daily for the duration of the experiment. Data are presented as mean ear thickness ±SEM. *P<0.01 by ANOVA. Results are shown in FIG. 12.

Figure 13:
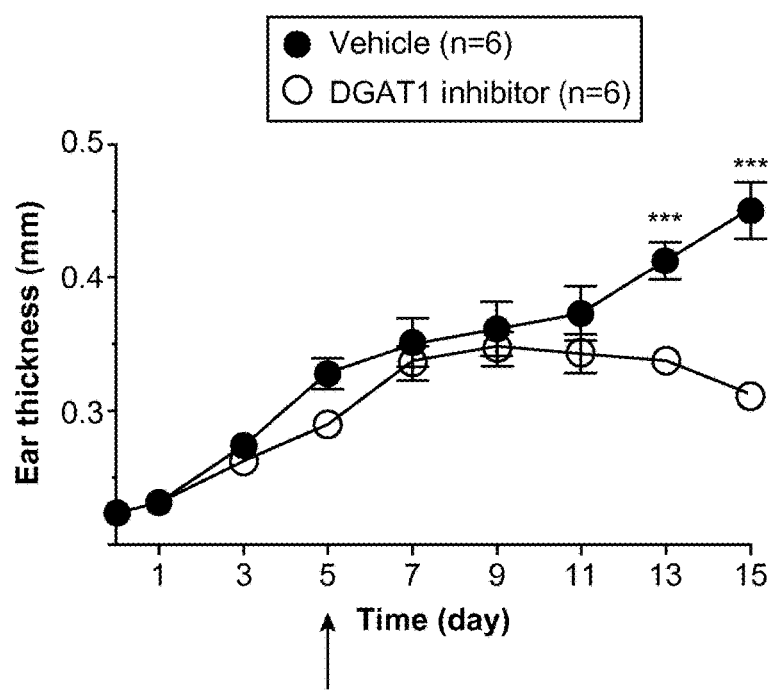
FIG. 13. Pharmacologic DGAT1 inhibition attenuates established IL-23-induced ear swelling.

Shown in FIG. 13, ears of male mice (8-15 weeks of age) were injected intradermally every other day with PBS or 500 ng recombinant IL-23. Beginning on day 5 (arrow), mice received 10 mg/kg of DGAT1 inhibitor A922500 (or 10% Captisol vehicle control) via subcutaneous injection. Mice continued to received drug or vehicle once daily for the duration of the experiment. Data are presented as mean ear thickness ±SEM. ***P<0.001 by ANOVA.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently

TABLE 2

Clinical EAE in mice treated with a DGAT1 inhibitor

| Treatment | Disease incidence | Mean maximal score (SEM) | Mean day of onset (SEM)[a] | No. of CNS inflammatory foci Meninges | Parenchyma |
|---|---|---|---|---|---|
| Vehicle | 10/10 (100%) | 2.5 (0.2) | 14.2 (0.4) | 41.2 (7.0) | 57.0 (9.6) |
| A922500 | 7/10 (70%) | 1.4 (0.4)[ns] | 20.1 (1.9)* | 19.8 (8.8) | 29.9 (12.4) |

Brain and spinal cord tissue was harvested from mice treated with DGAT1 inhibitor A922500 or 10% Captisol vehicle 30 days after induction of EAE by active immunization. Histological changes were evaluated as described in Methods; data are presented as mean (SEM).
[ns]not significant by Mann-Whitney U test (p = 0.05)
[a]Determined only for animals that developed EAE
*p < 0.01 by Student's t test known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method of treating multiple sclerosis in a subject with multiple sclerosis, the method comprising:
   administering to the subject with multiple sclerosis an effective dose of A922500, which inhibits DGAT1, wherein symptoms of multiple sclerosis are reduced.

2. The method of claim 1, wherein the effective dose of A922500 is effective in suppressing T cell activation in tissues affected by multiple sclerosis, and in suppressing progression of established disease.

3. The method of claim 1, wherein the effective dose of A922500 is effective in inducing regulatory T cells in tissues affected by multiple sclerosis, and in suppressing progression of established disease.

4. The method of claim 1, wherein the administration of the effective dose of A922500 to the subject with multiple sclerosis reduces relapse rate or disease progression.

* * * * *